US010755078B2

(12) United States Patent
Rubin et al.

(10) Patent No.: US 10,755,078 B2
(45) Date of Patent: Aug. 25, 2020

(54) METHODS AND DEVICES FOR LIVE CELL IMAGING ANALYSIS

(71) Applicants: President and Fellows of Harvard College, Cambridge, MA (US); Nikon Corporation, Tokyo (JP)

(72) Inventors: Lee L. Rubin, Wellesley, MA (US); Yasujiro Kiyota, Tokyo (JP); Chieko Nakada, Okamoto (JP); Keiichi Niikura, Kanagawa (JP); Kathleen L. Pfaff, Needham, MA (US)

(73) Assignees: President and Fellows of Harvard College, Cambridge, MA (US); Nikon Corporation, Tokyo (JP)

( * ) Notice: Subject to any disclaimer, the term of this patent is extended or adjusted under 35 U.S.C. 154(b) by 0 days.

(21) Appl. No.: 15/565,611

(22) PCT Filed: Apr. 8, 2016

(86) PCT No.: PCT/US2016/026833
§ 371 (c)(1),
(2) Date: Oct. 10, 2017

(87) PCT Pub. No.: WO2016/164857
PCT Pub. Date: Oct. 13, 2016

(65) Prior Publication Data
US 2018/0314876 A1  Nov. 1, 2018

Related U.S. Application Data

(60) Provisional application No. 62/183,703, filed on Jun. 23, 2015, provisional application No. 62/145,730, filed on Apr. 10, 2015.

(51) Int. Cl.
*G06K 9/00* (2006.01)
*C12M 1/34* (2006.01)
(Continued)

(52) U.S. Cl.
CPC ......... *G06K 9/00127* (2013.01); *C12M 41/46* (2013.01); *C12M 41/48* (2013.01);
(Continued)

(58) Field of Classification Search
CPC ............... A61K 31/235; A61K 31/635; A61K 2300/00; A61K 31/00; A61K 45/06;
(Continued)

(56) References Cited

U.S. PATENT DOCUMENTS 4,000,417 A  12/1976  Adkisson et al.
4,705,949 A  11/1987  Grimes, II et al.
(Continued)

FOREIGN PATENT DOCUMENTS

JP    3775223 B2    5/2006
JP    2013-236563 A  11/2013
(Continued)

OTHER PUBLICATIONS

Invitation to Pay Additional Fees dated Jun. 20, 2016 for Application No. PCT/US2016/026833.
(Continued)

*Primary Examiner* — Aklilu K Woldemariam
(74) *Attorney, Agent, or Firm* — Wolf, Greenfield & Sacks, P.C.

(57) ABSTRACT

Provided herein are methods for analysis of target cells on a population or individual basis, including before and after contact with a stimulus in order to determine the effect of such stimulus on the target cells. Also provided are devices for performing such methods. The analysis methods involve identifying and measuring or tracking morphological changes that occur in target cells over a period of time. Tracking is accomplished using imaging systems capable of imaging target cells individually over a period of time either continuously or at discrete intervals of time.

26 Claims, 20 Drawing Sheets

(51) Int. Cl.
    *C12N 5/0793*         (2010.01)
    *G01N 33/50*          (2006.01)
    *C12M 1/36*          (2006.01)
    *G06T 7/00*          (2017.01)

(52) U.S. Cl.
    CPC ....... C12N 5/0619 (2013.01); G01N 33/5026 (2013.01); G01N 33/5058 (2013.01); G06T 7/0012 (2013.01); *C12N 2501/13* (2013.01); *C12N 2501/415* (2013.01); *C12N 2501/727* (2013.01); *C12N 2501/999* (2013.01); *C12N 2506/02* (2013.01); *C12N 2506/45* (2013.01); *G01N 33/5091* (2013.01); *G01N 2500/10* (2013.01)

(58) Field of Classification Search
    CPC ............... A61K 48/00; G01N 33/5058; G01N 33/5005; G01N 2500/10; G01N 33/5091; G01N 15/1468; G01N 15/1475; G01N 2015/1415; G01N 2015/144; G01N 2015/1443; G01N 2015/1445; G01N 2015/1452; G01N 2015/1472; G01N 2015/149; G01N 33/5026; C12Q 2600/158; C07K 16/30; C12M 41/48; C12M 41/46; C12N 2506/02; C12N 2510/00; C12N 2501/13; C12N 2501/415; C12N 2501/727; C12N 2501/999; C12N 2506/45; C12N 5/0619; C12N 15/86; C12N 2740/13043; C12N 2740/13052; C12N 2840/20; C12N 2840/203; A61N 2005/067; A61N 5/062; A61N 5/1069; G06K 9/00127; G06K 9/6269; C40B 30/10; C40B 60/12; G06T 2207/30024; G06T 2207/10056; G06T 2207/20064; G06T 7/0014; G06T 7/42; G06T 2207/20084; G06T 7/0012; G06T 7/41
    USPC .......... 359/368, 391, 392, 372, 384; 435/29, 435/366, 325, 352, 374, 377, 455; 382/133, 128, 190
    See application file for complete search history.

(56) References Cited

U.S. PATENT DOCUMENTS

| | | | |
|---|---|---|---|
| 4,920,053 A | 4/1990 | Inoue et al. | |
| 4,958,920 A | 9/1990 | Jorgens et al. | |
| 4,974,952 A | 12/1990 | Focht | |
| 5,594,235 A | 1/1997 | Lee | |
| 5,733,925 A * | 3/1998 | Kunz | A61K 9/0024 514/449 |
| 5,861,985 A | 1/1999 | Ikoh | |
| 5,991,028 A | 11/1999 | Cabib et al. | |
| 6,005,964 A | 12/1999 | Reid et al. | |
| 6,017,761 A * | 1/2000 | Rigg | C12N 15/86 435/320.1 |
| 6,049,421 A | 4/2000 | Raz et al. | |
| 6,246,785 B1 | 6/2001 | Molnar et al. | |
| 6,804,385 B2 * | 10/2004 | Eisfeld | G06K 9/00127 359/368 |
| 6,834,238 B1 * | 12/2004 | Hochman | A61K 31/00 382/128 |
| 6,986,993 B1 | 1/2006 | Ghosh et al. | |
| 7,139,415 B2 | 11/2006 | Finkbeiner | |
| 7,223,556 B1 * | 5/2007 | Zhou | B82Y 5/00 435/68.1 |
| 8,828,721 B1 | 9/2014 | Hickman et al. | |
| 2003/0147881 A1 * | 8/2003 | Cheung | A61K 49/0004 424/131.1 |
| 2005/0113297 A1 * | 5/2005 | Francois | B82Y 5/00 424/155.1 |
| 2005/0261224 A1 * | 11/2005 | Kuchroo | A61P 13/12 514/44 R |
| 2006/0160068 A1 * | 7/2006 | Beechem | C07F 9/12 435/5 |
| 2006/0234250 A1 * | 10/2006 | Powers, III | C12Q 1/025 435/6.1 |
| 2008/0070303 A1 * | 3/2008 | West | A61K 35/30 435/377 |
| 2009/0075926 A1 * | 3/2009 | Bamdad | C07K 16/2863 514/44 R |
| 2009/0181881 A1 | 7/2009 | Mehlen et al. | |
| 2009/0227531 A1 * | 9/2009 | Eberwine | A61K 38/1709 514/43 |
| 2010/0002929 A1 * | 1/2010 | Sammak | G06K 9/00127 382/133 |
| 2010/0184033 A1 * | 7/2010 | West | C12N 5/0606 435/6.16 |
| 2010/0260406 A1 * | 10/2010 | Sammak | G06K 9/00127 382/133 |
| 2010/0284915 A1 * | 11/2010 | Dai | G01N 33/57415 424/9.1 |
| 2011/0003890 A1 * | 1/2011 | Schwartz | A61K 31/00 514/491 |
| 2011/0014701 A1 * | 1/2011 | Ghosh | C12N 5/0663 435/374 |
| 2011/0251130 A1 * | 10/2011 | Robertson | C07K 14/82 514/16.7 |
| 2013/0149287 A1 | 6/2013 | Livesey et al. | |
| 2013/0330761 A1 * | 12/2013 | Laing | G01N 33/574 435/29 |
| 2015/0010514 A1 | 1/2015 | Studer et al. | |
| 2015/0290233 A1 * | 10/2015 | Yarden | A61K 45/06 424/158.1 |
| 2016/0115444 A1 * | 4/2016 | Studer | C12N 5/0618 506/2 |
| 2016/0258958 A1 * | 9/2016 | Narain | G01N 33/57434 |
| 2018/0299478 A1 * | 10/2018 | Luthi | G01F 1/002 |

FOREIGN PATENT DOCUMENTS

| | | |
|---|---|---|
| WO | WO 2013/134499 A1 | 9/2013 |
| WO | WO 2014/172616 A2 | 10/2014 |

OTHER PUBLICATIONS

International Search Report and Written Opinion dated Aug. 26, 2016 for Application No. PCT/US2016/026833.

International Preliminary Report on Patentability dated Oct. 19, 2017 for Application No. PCT/US2016/026833.

Bahlmann et al., 4Pi-confocal microscopy of live cells. Ultramicroscopy. Apr. 2001;87(3):155-64.

Brennand et al., Modelling schizophrenia using hiPSC neurons. Nature. May 12, 2011;473(7346):221-5. doi: 10.1038/nature09915. Epub Apr. 13, 2011. Author Manuscript, 17 pages.

Guy et al., A fluorescence microscopy based genetic screen to identify mutants altered for interactions with host cells. J Microbiol Methods. Oct. 2000;42(2):129-38.

Irobi et al., Mutant HSPB8 causes motor neuron-specific neurite degeneration. Hum Mol Genet. Aug. 15, 2010;19(16):3254-65. doi: 10.1093/hmg/ddq234. Epub Jun. 10, 2010. Accessed Jul. 30, 2018 at https://www.ncbi.nlm.nih.gob/pme.articles/PMC2908473/, 20 pages.

Jin et al., Developmental changes in the responsiveness of rat spiral ganglion neurons to neurotrophic factors in dissociated culture: differential responses for survival, neuritogenesis and neuronal morphology. Cell Tissue Res. Jan. 2013;351(1):15-27. doi: 10.1007/s00441-012-1526-1. Epub Nov. 13, 2012. Author Manuscript, accessed Jul. 30, 2018 at https://www.ncbi.nlm.gov.pmc/articles/PMC3577061/, 22 pages.

Kam et al., Probing molecular processes in live cells by quantitative multidimensional microscopy. Trends Cell Biol. Aug. 2001;11(8):329-34.

Medlin, New microscope gives scientists the inside scoop on living cells. Environ Health Perspect. Nov. 1999;107(11):A566-8.

(56) References Cited

OTHER PUBLICATIONS

Nakada et al., Automated, non-invasive culture, and evaluation system for iPS cells under neural differentiation process [online]. ISSCR 10$^{th}$ Annual Meeting. 2012. [retrieved Aug. 2, 2016]. Available on the internet: https://www.nikoninstruments.com/Learn-Explore/Literature-Downloads/White-Papers/BioStation-CT/Neural-Differentiation-Analysis-ISSCR-2012-Poster>. 1 page.

Pre et al, A time course analysis of the electrophysiological properties of neurons differentiated from human induced pluripotent stem cells (iPSCs). PLoS One. Jul. 29, 2014;9(7):e103418(1-14). doi: 10.1371/journal.pone.0103418. eCollection 2014.

Rausch et al., A high-throughput screen for identifying transmembrane pore-forming peptides. Anal Biochem. Jun. 15, 2001;293(2):258-63.

Reynaud et al., Confocal microscopy: principles and applications to the field of reproductive biology. Folia Histochem Cytobiol. 2001;39(2):75-85.

Takazawa et al., Maturation of spinal motor neurons derived from human embryonic stem cells. PLoS One. ePub Jul. 3, 2012;7(7):e40154(1-9).

Ward et al., 96-Well plates providing high optical resolution for high-throughput, immunofluorescence-based screening of monoclonal antibodies against *Toxoplasma gondii*. J Immunol Methods. Nov. 19, 1999;230(1-2):11-8.

Yang et al., A small molecule screen in stem-cell-derived motor neurons identifies a kinase inhibitor as a candidate therapeutic for ALS. Cell Stem Cell. Jun. 6, 2013;12(6):713-26. doi: 10.1016/j.stem.2013.04.003. Epub Apr. 18, 2013, Author Manuscript, 22 pages.

Ziauddin et al., Microarrays of cells expressing defined cDNAs. Nature. May 3, 2001;411(6833):107-10.

Extended European Search Report dated Jan. 18, 2019 for Application No. EP 16777452.0.

Hofmann et al., Slice cultures of the imprinting-relevant forebrain area MNH of the domestic chick: quantitative characterization of neuronal morphology. Dev Brain Res. 1995;86:283-96.

\* cited by examiner

METHODS AND DEVICES FOR LIVE CELL IMAGING ANALYSIS

RELATED APPLICATIONS

This application is a national stage filing under 35 U.S.C. § 371 of International Application No. PCT/US2016/026833, filed Apr. 8, 2016, which was published under PCT Article 21(2) in English, and which claims the benefit under 35 U.S.C. § 119(e) of U.S. Provisional Application No. 62/145,730 filed Apr. 10, 2015, and U.S. Provisional Application No. 62/183,703 filed Jun. 23, 2015, both entitled "METHODS AND DEVICES FOR LIVE CELL IMAGING ANALYSIS", each of which is incorporated by reference herein in its entirety.

BACKGROUND OF INVENTION

The current drug discovery system for diseases of the nervous system (and most other disorders) relies heavily on animal models. Standard in vitro assays trying to identify drugs to treat neurodegenerative diseases employ single measurements of cell survival in which live healthy and diseased cells are counted after a fixed time period.

SUMMARY OF INVENTION

The drug discovery assays of the prior art are considered sub-optimal for a number of reasons. Animal models may only partially mimic the human disease they are intended to model. In addition, these in vivo models are inefficient both in terms of cost and time. In vitro assays typically only assess a single characteristic and then only once at or near the end of simulated disease progression. A classic example of this is assessment of cell viability (or alternatively cell death) following exposure to a drug or other stimulus. Such measurements fail to take into consideration earlier events that may be involved in or may be manifestations of disease onset and/or progression. They also do not take into account cell heterogeneity that exists in cell culture, including particularly in stem cell derived cultures.

The invention addresses various shortcomings of the prior art methods. The invention provides inter alia methods and devices for analyzing the effect(s) of one or more stimuli on a population of cells in vitro by identifying, assessing, and/or monitoring one or more changes in the population of cells over a period of time. Such changes may be morphological changes in target cells, including changes that can be detected, measured and monitored over time using an imaging system such as a microscope system. The invention further provides methods for evaluating status of a population of cells, according to one or more markers, and determining based on those markers the optimal time to contact the population of cells with a stimulus. Such methods are therefore individualized for a given population of cells (e.g., a cell line) in that stimulus is added only when a certain, typically pre-established, threshold is met. As discussed in greater detail below, the threshold may be a healthy or an unhealthy threshold.

The methods differ from the prior art methods in a number of ways. First, they measure an effect other than cell survival or cell death. The measured effect may be related to cell viability or it may not be related to cell viability. The latter situation is particularly helpful when the disease being studied is characterized by a dysfunction in a target cell population rather than by death of that target population. Second, the methods provided herein measure such effect over a length of time, whether continuously or at discrete time intervals, rather than at only a single time point at or near the end of the assay time-course. In this way, the methods provide a higher degree of resolution and understanding of earlier disease markers and the impact that various stimuli (including drug candidates) have on such markers. The ability to track earlier markers also potentially results in shorter assays, thereby increasing the efficiency of such assays both in terms of time and cost. Finally, tracking of earlier effects and the ability of a stimulus to impact an earlier event can lead to identification of stimuli (and potentially therapeutics) that can be used at early stages of disease progression, when impact may be greatest.

The invention therefore provides, in a general sense, screening methods (or screening assays) for determining the effect of a stimulus on a target cell population. These methods comprise the steps of obtaining a baseline measurement of a marker (such as a morphological marker) of a cell population, exposing the cell population to a stimulus, measuring the marker continuously or at discrete time intervals in order to identify and/or quantitate changes in the marker over time, wherein a change to the marker relative to baseline indicates the stimulus altered the development of the cell population.

In some embodiments, the cell population is a diseased cell population. Such populations may be patient-specific cell lines. In some instances, such cell lines may be generated through directed, lineage-specific, differentiation of patient-specific induced pluripotent stem cells (iPS cells).

In other embodiments, the cell population may be a control cell population, such as a cell line generated through directed, lineage-specific, differentiation of iPS cells from "normal" subjects. Normal subjects as used herein refer to subjects who do not have the disease of interest. The method described above may be performed by, additionally or alternatively, comparing change in the marker between the patient-specific target cell population and the normal cell population.

In some embodiments, the target cell population is neuron cell population such as a motor neuron (MN) cell population. The neuron and thus MN cell population may be generated through directed, lineage-specific, differentiation from patient-specific iPS cells. One or more markers in the MN cell population may be monitored pre- and post-exposure to a stimulus, whether continuously or at discrete intervals of time, and such pre- and post-exposure measurements may be compared to each other. Alternatively or additionally, they may be compared to marker measurements from normal cell populations, pre- and post-exposure to the same stimulus.

The cell populations, including the patient-specific cell population and the normal cell population may be grown in multi-chamber, such as multi-well, plates. Live cell imaging is then performed as a means to measure markers and thus changes to such markers in the cell population.

The cells of interest may be labeled with a detectable label in order to identify and distinguish them from other cells in the culture.

Thus, in one aspect, the disclosure provides a method comprising in vitro culturing a cell population, repeatedly obtaining images of target cells within the cell population over a period of time, either continuously or at discrete intervals of time, wherein the images detect single target cells, and detecting changes in a marker (or monitoring a marker) in the target cells based on analysis of the images.

In some embodiments, the target cells are motor neurons and the marker is node number per target cell. In some embodiments, the target cells are analyzed individually. In some embodiments, the method further comprises culturing the cell population until a percentage of target cells having a defined phenotype is present. In some embodiments, the defined phenotype is a healthy phenotype. In some embodiments, the defined phenotype is an unhealthy phenotype.

In still another aspect, this disclosure provides a method comprising contacting target cells in a cell culture with a stimulus, wherein the target cells are present in a heterogeneous population of cells, repeatedly obtaining images of the target cells over a period of time, either continuously or at discrete intervals of time, and detecting changes in a marker in the target cells based on analysis of the images.

In some embodiments, changes in the marker are determined by measuring and comparing the marker pre- and post-exposure to the stimulus. In some embodiments, the time it takes for such marker changes to occur is measured (e.g., the time between when the cells are contacted with a stimulus and the time the marker changes are apparent, whether in one a cell or a sufficient number of cells), and optionally such time is compared to a similar time measurement in other populations, such as similar target cells from another patient or source.

In some embodiments, changes in the marker are determined by measuring and comparing the marker post-exposure to the stimulus in both normal and diseased target cells.

In some embodiment, the target cells are cells that grow in an adherent manner in culture, and which optionally grow in a monolayer in culture.

In some embodiments, the target cells are motor neurons. In some embodiments, the target cells are obtained by in vitro differentiation of pluripotent stem cells. In some embodiments, the pluripotent stem cells are induced pluripotent stem cells derived from human subjects having a neurological disorder. In some embodiments, wherein the neurological disorder is spinal muscular atrophy or amyotrophic lateral sclerosis.

In some embodiments, the target cells are cortical neurons derived from human subjects having autism or Alzheimer's Disease.

In some embodiments, the target cells are dopaminergic neurons derived from human subjects having Parkinson's disease.

In some embodiments, the marker is number of nodes per target cell. As used herein, a node is the physical location between the neuron cell body and a neurite (such as a dendrite or an axon). Thus, in some instances, the node may be representative of the number of neurites extending from a neuron.

In some embodiments, the marker is a decrease in the number of nodes per target cell to a number below 3.

In some embodiments, the target cells are contacted with the stimulus once at least 50% of target cells contain 3 or more nodes per target cell. The stimulus may be a chemical, electrical, electromagnetic (e.g., radiation), physical (e.g., mechanical) or other type of stimulus. Chemical stimuli include small chemical molecules as that term is understood in the art; nucleic acid based agents such as siRNA or other RNA interference agents; amino acid or protein based agents such as antibodies, antibody fragments, peptides, and the like; carbohydrates, lipids, and the like. The chemical stimulus may be defined functionally. For example, it may be a ligand for a known receptor such as a cell surface receptor having enzymatic activity, or a receptor for a known ligand such as a cell surface ligand, a hormone, a transcriptional or translational mediator, an agent that impacts cell division or DNA replication, and the like. In some embodiments, the stimulus is a chemical compound known or suspected to have effects on neurons, and the method tests the effect of such stimulus.

In some embodiments, the target cells are detectably labeled.

In some embodiments, the images are obtained using phase contrast and fluorescence microscopy.

In some embodiments, the images are obtained continuously. In some embodiments, the images are obtained at discrete intervals.

In some embodiments, the method further comprises measuring the time between when target cells are contacted with the stimulus and when marker changes are detected including when marker changes are first detected and/or when marker changes are detected in a threshold percentage of cells (e.g., in at least 10%, 20%, 30%, 40%, 50%, 60%, 70%, 80%, 90%, or 100% of the cells).

In some embodiments, target cells derived from other human subjects are concurrently analyzed.

In some embodiments, target cells derived from different human subjects are contacted with the stimulus at different times, depending on the status of target cells.

In some embodiments, the marker is not cell viability or cell survival. In some embodiments, the marker is a marker of cell health. In some embodiments, the marker is associated with dysfunction or cell death.

In some embodiments, the images are repeatedly obtained over a period of 7 days, or 14 days, or longer. In some embodiments, the images are repeatedly obtained every hour, every two hours, every 6 hours, every 12 hours, or every 24 hours.

In some embodiments, the target cells are monitored pre-exposure to the stimulus in order to determine an appropriate time for stimulus exposure. In some embodiments, an appropriate time for stimulus exposure is a time at which at least 10%, 20%, 30%, 40%, 50%, 60%, 70%, 80%, 90% or 100% of the target cells that are neurons have three or more nodes.

In some embodiments, the appropriate time for stimulus exposure is a time at which a threshold number of target cells are present in the culture. For example, the appropriate time may be when at least 10, 25, 50, 100, 250, 500, 1000, 5000, 10,000 or more target cells are present within a given cell population (e.g., within a single patient-specific cell population, which optionally may be present in one well or one chamber of a multiwall or multi-chamber container). Thus, in some embodiments, the method may further comprise repeatedly obtaining images of the cell culture over a period of time prior to contact of the culture with the stimulus, either continuously or at discrete intervals of time, in order to identify and optionally quantitate target cells in the culture.

Certain methods of this disclosure comprise identifying and measuring the number of target cells in a culture prior to and after contact of the culture with a stimulus. As described in greater detail herein, a target cell may be defined for example as a neuron having 3 or more nodes (as those structures are defined herein), and thus the method may comprise measuring the number of neurons having 3 or more nodes prior to contact with a stimulus, measuring the number of neurons having 3 or more nodes after contact with a stimulus, and comparing such numbers to determine the effect of the stimulus on neuron health. In this way, the method identifies a number of neurons and characterizes them as group, and the stimulus is characterized by its effect on the group of neurons.

Alternatively, the method can be performed by identifying and tracking one or more neurons in an individual manner. For example, any given neuron can be monitored for a period of time, whether continuously or at discrete time points, including before and after exposure to a stimulus. The effect of the stimulus on the neuron can then be assessed at a single cell level. Such effect may be a change in the number of nodes, a change in the number of neurites, the time it takes for any such change to occur, the time it takes for the neuron to transition from a healthy state (e.g., having 3 or more nodes) to an unhealthy state (e.g., having less than 3 nodes), the time it takes for loss of a node (or neurite), etc. Additionally, the method may be used to monitor neurons having less than 3 nodes prior to stimulus exposure and to determine the effect of the stimulus on such neurons.

The invention further provides in yet another aspect a kit comprising cells to be used in a screening assay as described herein, including pluripotent cells from which the cells are derived, reagents used to derive the cells from the pluripotent cells if appropriate, culture vessels to grow the cells, instructions for use, and optionally a detection system as described herein.

These and other aspects and embodiments will be described in greater detail herein.

BRIEF DESCRIPTION OF DRAWINGS

FIG. 6A shows an exemplary non-limiting 28 day differentiation process for deriving motor neurons from human embryonic stem cells (hESCs). The differentiated progeny are then plated and subjected to the trophic factor(s) (TF) withdrawal test (either on Day 4, the early time point, or on Day 8, the late time point) or the MG132 (proteasome inhibitor) test (from Day 4 to Day 10). The end point of this analysis was Day 19. FIG. 6B shows the monitoring of the cells using live imaging on the BioStation CT. FIG. 6C shows video time lapse phenotypic analysis, with respect to three descriptors: the number of cell bodies, the neurite length, and the number of nodes per cell. FIG. 6D shows the classification of neurons by the number of nodes: in this instance "healthy" neurons were classified as those having more than three nodes, whereas unhealthy or dying neurons had progressively fewer nodes. FIG. 6E shows further motor neurons classification based on changes in the number of nodes through long term single cell tracking. Starting from a healthy (H) state, the neuron has three potential outcomes: healthy end (denoted HH), unhealthy end (denoted HU), or dying end (denoted HD). As shown in the lower right graph of FIG. 6E, the majority of motor neurons that begin in a healthy state end the protocol in a healthy state (denoted HH) in an exemplary culture without stress.

DETAILED DESCRIPTION OF INVENTION

Figure 1A:
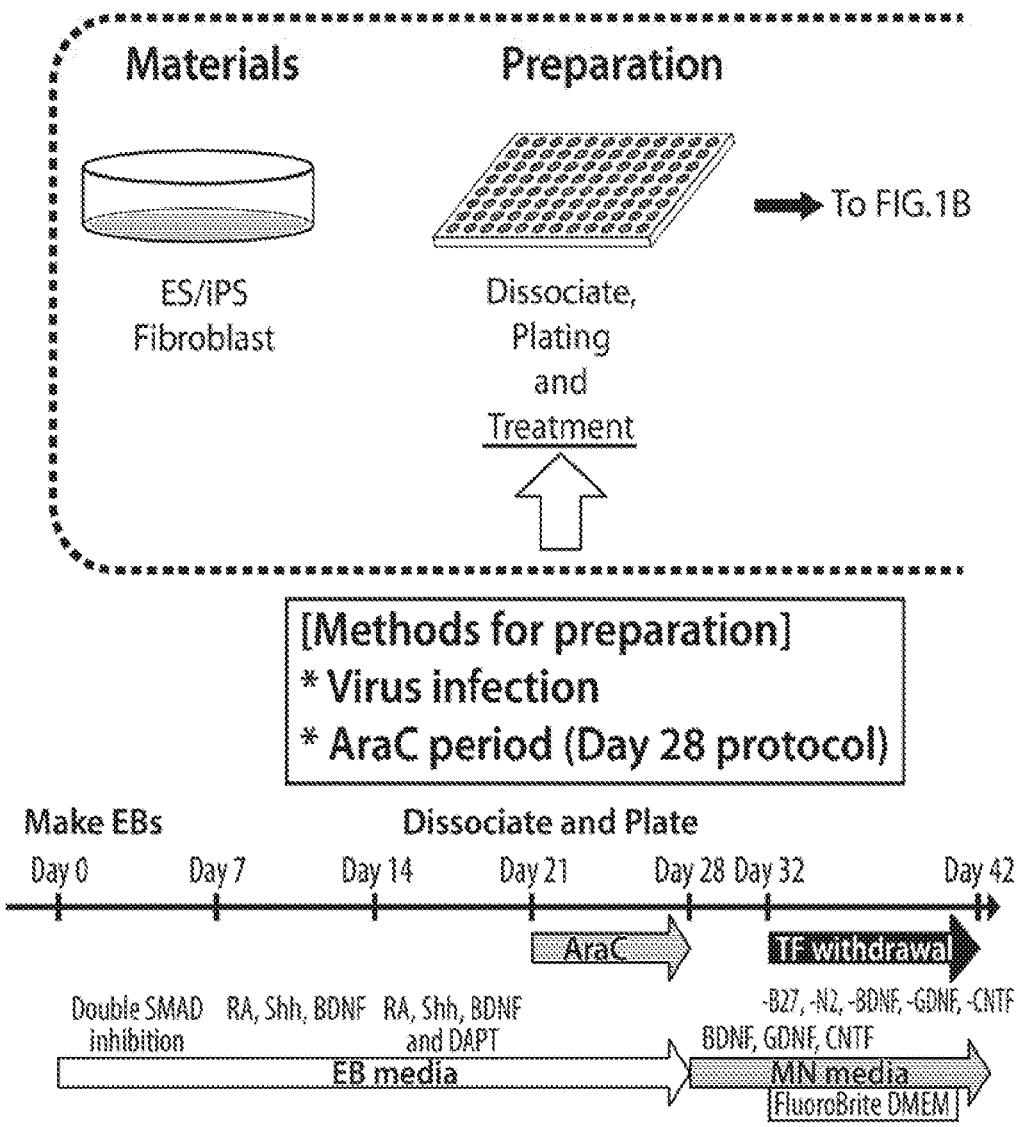
FIGS. 1A-1C show a schematic overview of the screening methods provided in this disclosure. These methods, and the results generated therefrom, are more consistent and stable than prior art methods. The Figure illustrates the various steps in the process, including preparation of the cell population including labeling of the cells of interest with a detectable label (FIG. 1A), time-lapse, live cell imaging and analysis of the cells to identify a marker of interest and make a baseline measurement for such marker, exposure of the cell population to a stimulus, further time-lapse, live cell imaging and analysis of the cells to make further measurements of the marker (FIG. 1B), and output of results (FIG. 1C).

The invention provides, in part, a method to analyze human patient-specific and control iPS cell derived neurons grown in cell culture. As described herein, live cell imaging was used to visualize changes, including early and late changes, in neurons such as motor neurons over significant time periods. This new method may be used to: (a) discover cellular changes that occur in neurons very early in a disease process; (b) study many different types of cells in heterogeneous cultures by tracking single cells; (c) establish assays based on robust detection of early phenotypes; (d) screen for and test potential therapeutics that act to block these early steps at a time when the cells are still relatively healthy. The invention relates to methods of producing neurons, plating them in multiwell plates, culturing them throughout a period of time in an environment conducive to their growth, development, proliferation, etc. while still maintaining the capability to live-image the cells, whether continuously or at discrete intervals of time (as can be accomplished using for example a Nikon BioStation CT), using phase and fluorescence imaging to measure many features of individual cells, quantifying how those features change over time and analyzing the data collected from large numbers of single cells over time.

The ability to analyze the target cell population of interest also allows an end user to determine the most appropriate time for stimulus exposure. This is due to the variability that can occur between cell populations. As discussed herein, when the method is used to analyze a number of different cell populations (e.g., a number of patient-specific samples being analyzed simultaneously, as in a high-throughput screening assay), then the ability to control the timing of stimulus exposure on a sample-to-sample basis provides analysis that is more fine-tuned and of higher resolution. Put another way, the methods provided herein allow an end user to identify a proper "start" time and "stop" time for the assay, even if such start and stop times vary between samples. The ability to identify and thus vary the start time (e.g., the time of stimulus exposure) between samples means the samples are being treated in a more biologically consistent manner (e.g., at the same time point in their development and/or progression) rather than at a time when some samples are developmentally delayed or advanced relative to the average.

The various methods provided herein may be performed on a single cell basis, intending that in some embodiments the methods track a single cell, such as a single motor neuron, determine when the single cell has met a threshold, contact the cell with a stimulus, and then continue to track the cell following stimulus contact. The threshold may be a phenotype associated with a healthy (or normal) cell, such phenotype being referred to herein as a healthy or normal phenotype). Alternatively, the threshold may be a phenotype associated with an unhealthy (or diseased) cell, such phenotype being referred to herein as an unhealthy or diseased phenotype. Thus, the cell may be a normal cell or a diseased cell. The diseased cell may be but is not limited to a cell harboring a mutation associated with a particular condition such as a neurodegenerative condition. The diseased cell may be but is not limited to a cell produced by the in vitro differentiation of pluripotent cells (e.g., iPS cells) derived from a subject having a neurodegenerative condition.

Thus, in some embodiments, the method is used to track a cell having a healthy phenotype, after contact with a stimulus for a period of time. The period of time may be the time it takes for the phenotype to change to an unhealthy phenotype, as a result of stimulus contact. Such time may be referred to herein as a "healthy time". The healthy phenotype may be a node number of equal to or greater than 3. In this manner, stimuli that have potentially detrimental or degenerative effect may be identified using this in vitro screen.

Alternatively, the method may be used to track a cell having an initially unhealthy (or diseased) phenotype, after contact with a stimulus for a period of time. The period of time may be the time it takes for the phenotype to change to a healthy phenotype, as a result of stimulus contact. Such time may be referred to herein as a "recovery time". The unhealthy phenotype may be a node number that is less than 3, and a healthy phenotype may be a node number that is equal to or greater than 3. In this manner, stimuli that have potentially therapeutic benefit may be identified using this in vitro screen. Moreover, stimuli having potentially therapeutic benefit for cells from a particular patient may be identified, thereby leading to an personalized therapeutic.

The periods of time may be on the order of days, or weeks, or in some instances months. One advantage of the disclosed screening methods is the ability to assess effect of a stimulus on a shorter time scale than might otherwise be possible using prior art methods. In some instances, the period of time may be about 2 weeks.

It is to be understood that the method may be used to track a plurality of single cells, wherein each of the single cells is tracked separately from all other cells in the plurality. In this way, the method is used to obtain information from a number of cells, although without reverting to a population-based analysis.

It is also to be understood that the method may be used to study the effect of a stimulus on different pluralities of cells. For example, if each of the pluralities is a cell line or derives from a particular cell line, then the method may be used to study a number of different cell lines (or their progeny) simultaneously, all the while still performing a single cell analysis. In this way, the cell lines may be contacted with a stimulus at different times, relative to each other, such time of contact dictated by when each line has met a particular threshold, including for example having a threshold number of cells with the particular threshold. This can be carried out using a healthy or an unhealthy phenotype as the starting point for stimulus contact.

It will be further understood that the methods may be used to study a number of different cell populations (e.g., cell lines) simultaneously against a single stimulus, or alternatively to study a number of different stimuli against a single cell population (e.g., a cell line).

The phenotype may be defined by one or more markers including for example morphological or structural characteristics, functional characteristics, physiological characteristics, viability or cell death markers, and the like. The particular markers used will depend on the cell type being tracked and studied. Specific examples include motility, electrical activity, including calcium-based activation, and the like. In the case of motor neurons, the phenotype may include number of nodes, size and/or shape of cell bodies, and/or neurite length. Such markers are superior to for example tracking cell viability or cell death, particularly since in some instances the effect of a stimulus may not be cell survival or cell death at all, and rather may be cell dysregulation.

As will be apparent based on this disclosure, the methods provided herein are useful for standardizing heterogeneity between cell populations as well as heterogeneity within a cell population. Standardization between cell populations is achieved by tracking cell populations separately and initiating stimulus contact only once a threshold is met. Standardization within a cell population is achieved by tracking individual cells within the population.

The cells of interest may be labeled with a detectable label in order to identify and distinguish them from other cells in the culture. As an example, the cells may be fluorescently labeled by inducing expression of a fluorescent label (such as GFP) under the control of a lineage-specific promoter/enhancer. Such labeling methods are known in the art. Examples are provided herein and can also be found by reference to U.S. Pat. No. 7,139,415, the specific teachings of which relating to detectably labeling cells are incorporated by reference herein.

This is particularly useful if the target cell population is heterogeneous and comprises other cell types. For this additional reason, the methods provided by this disclosure are able to provide better resolution regarding effects of a stimulus on a defined cell type, as compared to prior art methods that analyze bulk cell populations, including cell survival or viability (or other readout) of a heterogeneous population rather than a defined subpopulation more tailored to the population of interest.

More specifically, we performed the methods described herein on stem cell derived motor neurons (MN). We performed these methods on human embryonic stem (hES) cell lines that stably express fluorescent reporters under the control of the Hb9 or Islet promoter, thereby specifically labeling MNs relative to all other cells in the culture. We then extended these analyses to iPSC-derived MN cultures that are infected with a lentiviral fluorescent reporter, driven either by the MN-specific Hb9 promoter or by the pan-neuronal Synapsin promoter. We developed and utilized an automated MN detection algorithm that identifies all cell bodies based on size and fluorescence intensity.

The detection algorithm is also able to identify the neurites, the narrow processes that extend from the cell body of a neuron (such cell body also referred to as a soma), and to identify the "node" or the junction between the cell body and the neurites. Neurite is used to describe either a dendrite or an axon. When the neurite is an axon, the node may be the axon hillock. Motor neuron cultures were analyzed in real time to determine the relative developmental stage or maturity of a sample (e.g., a particular patient-specific population of motor neurons) by counting nodes. It is recognized in the art that there is inherent variability in differentiation efficiency and time line (within a cell line and between cell lines). The methods provided herein may minimize the impact of this variability on an experiment. For example, the algorithm stipulates that cells with 3 or more nodes are true MN. The parameter is then used in the methods provided herein as an indicator of an MN, whether at the beginning of the culture (e.g., to demarcate a start time) or as a readout throughout the analysis (e.g., to assess the effect of a stimulus). When used at the beginning of the analysis, the algorithm may be employed to ensure there is a sufficient number of MN before exposing the culture to a stimulus. The algorithm is described in greater detail below. The parameter of 3 or more nodes is referred to herein as a threshold at or above which cells may be scored as healthy and below which cells may be scored as not healthy.

We further developed a robust cell-tracking algorithm, which may be used to reliably identify target cells and study their movement and morphological changes over time. By combining node identification, as described above, with the ability to track cells over time, it was possible to compare the behavior of MN in basal versus stressed conditions (as may result from exposure to some stimuli). By defining cells having 3 or more nodes as "healthy" MNs, and repeatedly assessing the number of healthy MNs over time and/or tracking cells denoted as healthy at the outset of the analysis, it was possible to measure the length of time cells are healthy in culture. For example, in some embodiments, the method involves identifying healthy MNs at the outset, tracking such healthy MNs with time, and measuring the time at which such previously healthy cells are no longer considered healthy according to the aforementioned parameters (i.e., they no longer have 3 or more nodes). This period of time between the start of the analysis (to) and the time at which the cells are no longer healthy is referred to herein as "healthy time" or HT. The "healthy time assay" provided herein may be used across biological samples and between different stimuli in order to more accurately compare the effect of stimuli and/or the response of cells to such stimuli. The algorithm is described in greater detail below.

The live cell analysis approach provided herein may provide one or more advantages over traditional survival studies, which typically only measure a single time point. For example, using the methods provided herein, it may be possible to detect early changes in cellular morphology that precede cell death. Such changes may be novel changes and/or changes not previously associated with cell death or not identified as being early markers of cell death. As another example, the methods provided herein may allow the classification of subpopulations of cells based on their relative stage of differentiation or morphological characteristics at the time of exposure to a stimulus. As yet another example, the methods provided herein may be used to collect information over the life-time of a cell or cells.

Additionally, these methods and analyses may be used to identify novel therapeutic agents for the disease of interest, including neurodegenerative diseases.

Methods for directed, lineage-specific, differentiation of pluripotent stem cells such as but not limited to iPS cells are known in the art. Reference can be made to for example "Human Embryonic Stem Cells: The Practical Handbook", Eds. Sullivan, Cowan and Eggan, Wiley, 2007.

Stimuli according to this disclosure may be any chemical, electrical, electromagnetic, mechanical or other agent that can be contacted with target cells and which may be tested for its effect on target cells such as neurons. In some embodiments, the stimulus is a chemical agent (referred to herein as a drug) and the methods are used to determine the effect of the agent on the target cells. In some embodiments, the methods are used to determine the ability of an agent to block other effects induced in the target cells. In some embodiments, more than one stimulus may be contacted with the target cells, such as for example a plurality of agents from for example a library.

These and other aspects and embodiments of the invention are described below in greater detail.

As discussed above, the methods provided herein involve long-term live cell imaging of in vitro derived neurons from pluripotent stem cells such as embryonic stem cells (ESCs) or induced pluripotent stem cells (iPSCs). These methods have the potential to be a novel platform for drug discovery in neurodegenerative disease. Time-lapse analysis of neurons during differentiation, survival, stress response and/or death has several advantages, including the ability to identify early morphological changes that accompany disease-associated processes. Further, single cell tracking can compensate for the morphological heterogeneity inherent in stem cell-derived cell cultures. We have conducted detailed long-term analysis of individual stem cell-derived motor neurons (MNs) from early times after their differentiation until their death. Experiments were carried out using a Nikon BioStation CT, however other imaging systems having similar robust cell tracking capabilities can be used to follow individual MNs. Imaging analysis algorithms were developed to track key attributes such as cell body size and/or shape, neurite number and neurite length. We used these imaging tools to study MNs subjected to two different stressors that mimic disease-like circumstances: (1) neurotrophic factor (TF) withdrawal and (2) treatment with the proteasome inhibitor MG132. By analyzing many MNs, we have defined a new, morphological predictor for cell death that involves careful measurement of neuritic changes. This analysis algorithm determines the "healthy time (HT)" for each MN, and this measurement reveals the kinetics of survival responses that are not apparent with endpoint analysis. Quantifying disrupted neurites as an index of disease onset is advantageous since these changes occur early in the death process and appear to provide greater sensitivity than that seen by counting surviving cells.

Similar studies can be performed using diseased MNs derived from Spinal Muscular Atrophy and Amyotrophic Lateral Sclerosis (ALS) patient samples, or using other disease-relevant neuron populations, such as cortical neurons (affected in autism and Alzheimer's Disease) and dopaminergic neurons (affected in Parkinson's Disease). These analyses may be useful in uncovering new classes of therapeutic molecules with potential for intervening early in the progression of these diseases.

Timing of Exposure to Stimuli

As discussed above, when using cells originating from stem cells or somatic cells to evaluate drug efficacy while inducing the differentiation of the cells, the state of differentiation and the degree of maturity of the cells are known to be dependent on the origin of the cells and/or the culture conditions. In addition, when evaluating the efficacy of a given drug, it is known that the drug response due to the state of differentiation and the degree of maturity of the cells.

Due to the factors described above, the proper timing for adding a drug whose drug efficacy is to be confirmed should differ depending on the origin of the cells and/or the culture conditions. However, with conventional evaluation methods, it is impossible to know such a proper timing for adding a drug, and it has not been possible to evaluate drug efficacy with high precision.

This disclosure provides, inter alia, a determination device, an observation system, and a program thereof, a cell production method, and cells produced by the production method.

One aspect provides a determination device comprising:

a calculation part for calculating a value based on a number of cell bodies having at least a predetermined number of nodes out of the cell bodies contained in an image of cells in culture and comprising cell bodies and nodes, the predetermined number of nodes corresponding to a type of cells;

a first determination part for determining whether the value calculated by the calculation part satisfies a predetermined condition corresponding to a user input; and an output part for outputting information indicating a timing for administering the drug if the first determination part determines that the value satisfies the predetermined condition.

Node is defined as the connection part of cell body and liner structure.

This disclosure additionally provides, inter alia, an observation system comprising an imaging part for imaging a region containing the cell bodies in culture and the determination device described above.

This disclosure additionally provides a program for making a computer execute the following:

a calculation step of calculating a value based on a number of cell bodies having at least a predetermined number of nodes out of the cell bodies contained in an image of cells in culture and comprising the cell bodies and the nodes, the predetermined number of nodes corresponding to a type of cells;

a first determination step of determining whether the value calculated by the calculation step satisfies a predetermined condition corresponding to a user input; and an output step of outputting information indicating a timing for administering the drug if it is determined by the first determination step that the value satisfies the predetermined condition.

This disclosure additionally provides a cell production method comprising:

a calculation step of calculating a value based on a number of cell bodies having at least a predetermined number of nodes out of the cell bodies contained in an image of cells in culture and comprising the cell bodies and the nodes, the predetermined number of nodes corresponding to a type of cells;

a first determination step of determining whether the value calculated by the calculation step satisfies a predetermined condition corresponding to a user input; and an output step of outputting information indicating a timing for administering the drug if it is determined by the first determination step that the value satisfies the predetermined conditions.

As will be described in greater detail herein, the disclosure provides methods that may be used to improve the precision of drug response evaluation.

Various devices and systems that may be used to carry out the methods and analyses described herein will now be described.

An incubator (observation device) 11, for example, calculates an index of the differentiation or maturity of cells constituted by cell bodies having linear structures, the cells being cultured from stem cells such as iPS (induced pluripotent stem) cells or ES (embryonic stem) cells, and then outputs information indicating the timing for administering a drug corresponding to the drug to be administered to the cells based on the calculated index. As a result, the incubator 11 is able to uniform the timing of drug administration to a proper administration timing and, as a result, improve the precision of drug efficacy evaluation. Hereafter, the proper administration timing refers to an administration timing with which the efficacy of an administered drug is high, for example, but may also refer to another timing. In addition, cells having linear structures refer to cells constituted by cell bodies having neurites or dendrons, for example.

In addition, the incubator 11 determines the state of cells based on the calculated index, and outputs information indicating the state if the determined state has changed from the previously determined state. As a result, the incubator 11 is able to prevent users from overlooking changes in the state of cells. The state of cells refers a state classified by the degree of maturity of the cells or a state classified by the stage of differentiation of the cells, for example. In one example, a case in which the incubator 11 determines a state classified by the degree of maturity of the cells as the state of the cells will be described.

Hereafter, a state classified by the degree of maturity of cells will be simply called the state of cells for the sake of convenience. In addition, the following description will emphasize neurons, including motor neurons, as the cells of interest. Further, the cells constituted by cell bodies having linear structures may instead be other types of cells. That is, the incubator 11 may have a configuration in which the processing described below is applied to other cells cultured from stem cells instead of a configuration in which the processing is applied to cells.

Figure 2:
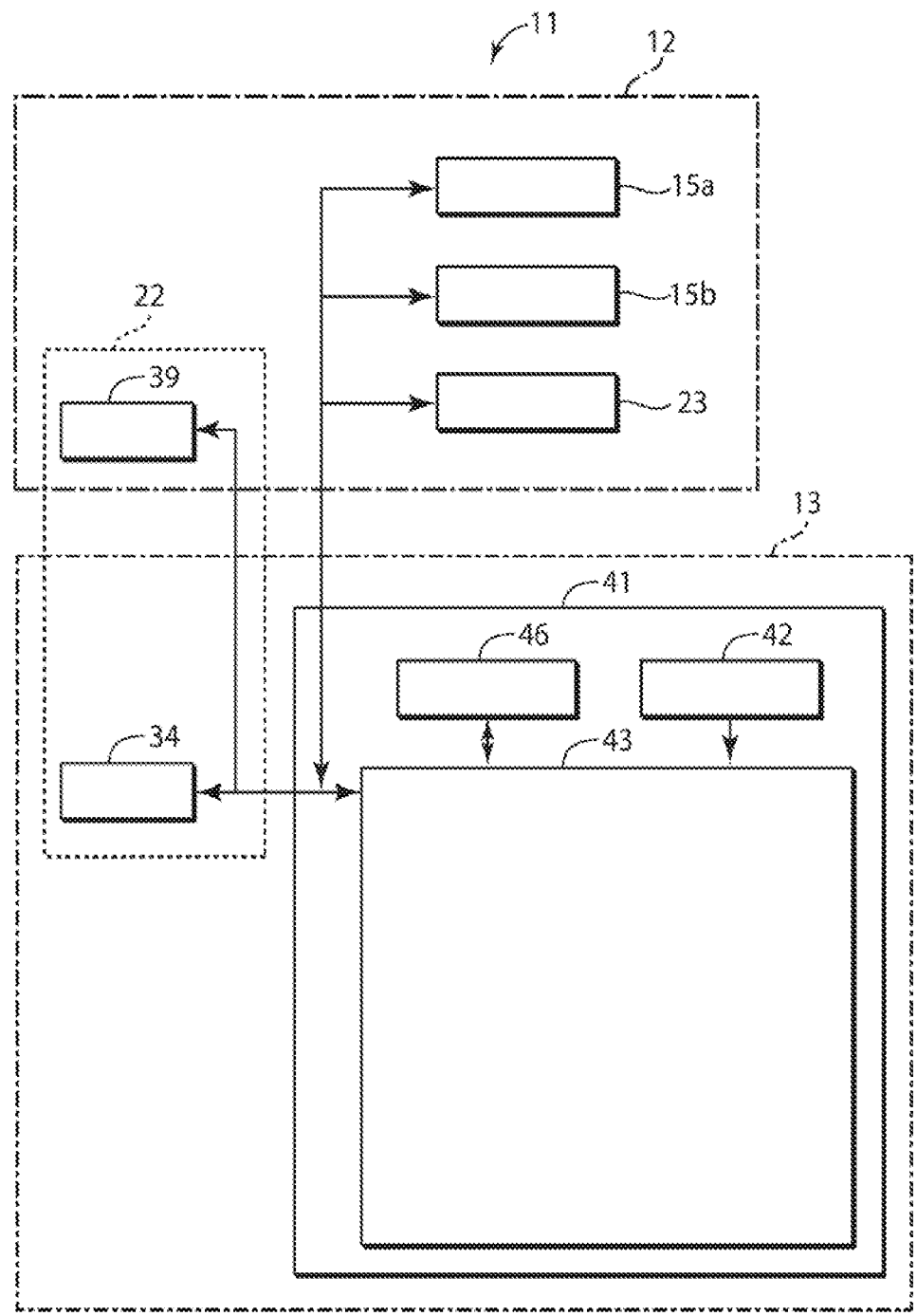
FIG. 2 is a block diagram that illustrates an example of a configuration of the observation device as provided herein.
Figure 3:
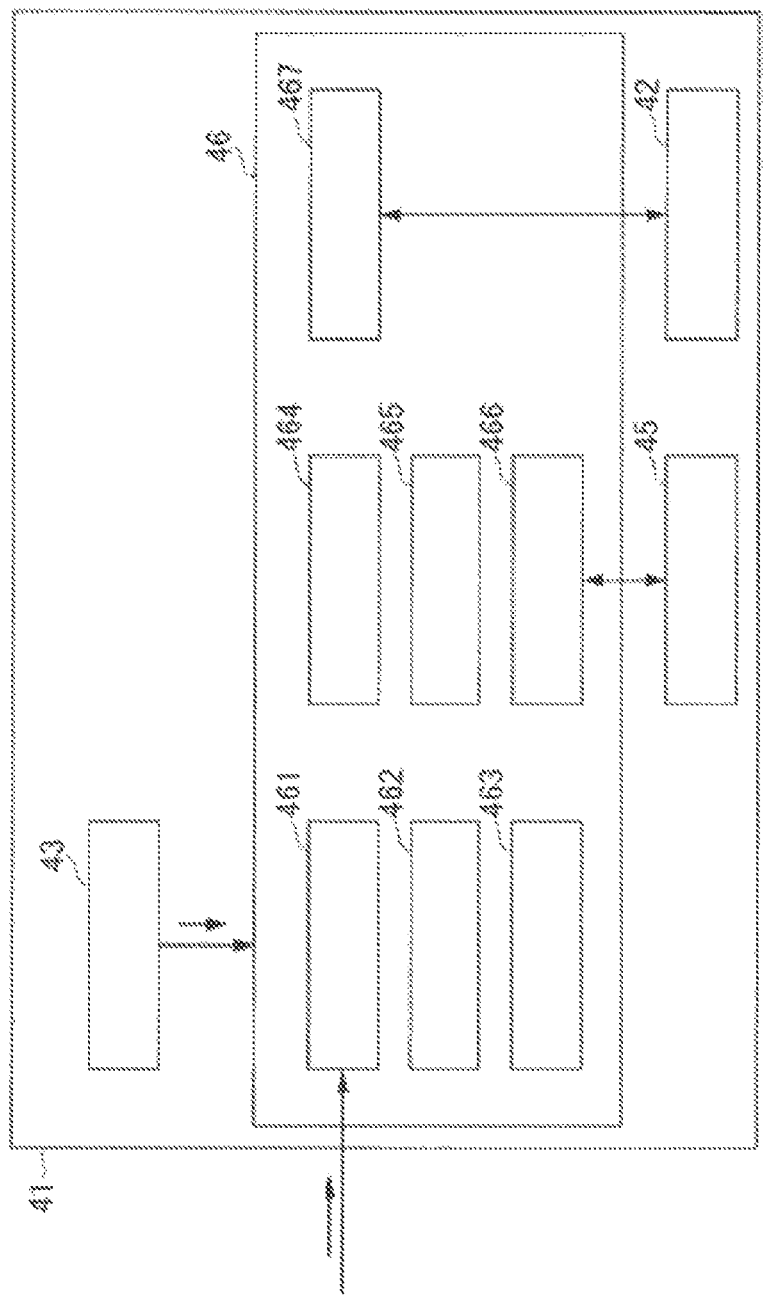
FIG. 3 is a block diagram illustrating an example of a configuration of a control device of the observation device provided herein.

An overview of the configuration of the incubator 11 according to an embodiment of the present invention will be given hereinafter with reference to FIG. 2. FIG. 2 is a block diagram illustrating an example of the configuration of the incubator 11 of one embodiment. FIG. 3 is a block diagram illustrating an example of the configuration of a control device 41 of the incubator 11 of this embodiment.

This incubator 11 is a device for culturing cells as well as observing the state of cells by imaging the cultured cells with a microscope camera. The incubator 11 has an upper casing 12 and a lower casing 13. In the assembly state of the incubator 11, the upper casing 12 is mounted on the lower casing 13. In addition, the internal space of the upper casing 12 and the lower casing 13 is partitioned vertically by a base plate 14.

First, an overview of the configuration of the upper casing 12 will be given. A constant-temperature chamber 15 for culturing cells is formed inside the upper casing 12. This constant-temperature chamber 15 has a temperature adjustment device 15a and a humidity adjustment device 15b, and the inside of the constant-temperature chamber 15 is maintained at an environment suitable to culturing cells (for example, an atmosphere with a temperature of 37° C. and 90% humidity).

A large door 16, a middle door 17, and a small door 18 are disposed on the front surface of the constant-temperature chamber 15. The large door 16 covers the front surfaces of the upper casing 12 and the lower casing 13. The middle door 17 covers the front surface of the upper casing 12 and isolates the environment between the constant-temperature chamber 15 and the outside when the large door 16 is open. The small door 18 is a door for inserting and removing a culture vessel 19 for culturing cells and is attached to the middle door 17. By inserting and removing the culture vessel 19 from the small door 18, it becomes possible to suppress changes in the environment of the constant-temperature chamber 15. In addition, the large door 16, the middle door 17, and the small door 18 are respectively kept in an airtight state by gaskets P1, P2, and P3.

Further, the constant-temperature chamber 15 is provided with a stocker 21, an observation unit 22, a vessel conveying device 23, and a conveying stand 24. Here, the conveying stand 24 is disposed in front of the small door 18 so as to insert and remove the culture vessel 19 from the small door 18.

The stocker 21 is disposed on the left side of the constant-temperature chamber 15 from the perspective of the front surface of the upper casing 12. The stocker 21 has a plurality of shelves so that a plurality of culture vessels 19 can be stored on each of the shelves of the stocker 21. In addition, cells to be cultured (neurons in this example) are housed in each of the culture vessels 19 together with a culture medium. The stocker 21 is not an essential component.

The observation unit 22 is disposed on the right side of the constant-temperature chamber 15 from the perspective of the front surface of the upper casing 12. This observation unit 22 makes it possible to execute a time-lapse observation of the cells inside the culture vessel 19.

Here, the observation unit 22 is disposed so as to be fitted into an opening of the base plate 14 of the upper casing 12. The observation unit 22 comprises a sample stand 31, a stand arm 32 provided with an illuminated light source projecting upward from the sample stand 31, and a main body portion 33 with a built-in observation optical system and an imaging device 34. The sample stand 31 and the stand arm 32 are disposed in the constant-temperature chamber 15, and the main body portion 33 is housed inside the lower casing 13.

The sample stand 31 is made of a translucent material, and the culture vessel 19 can be placed thereon. The sample stand 31 is configured so as to be movable in the horizontal direction so that the position of the culture vessel 19 placed on the upper surface thereof can be adjusted. In addition, an LED light source 39 is built into the stand arm 32. The imaging device 34 is able to obtain a microscopic image of cells by imaging the cells of the culture vessel 19 trans-illuminated from the upper side of the sample stand 31 by the stand arm 32 via a microscopic optical system. In this example, this microscopic image is a fluorescent image taken after the cells in the culture vessel 19 are fluorescently stained or are transfected by fluorescent protein, but the image may be another image such as a phase difference image as long as cell bodies and nodes can be detected from the image.

The vessel conveying device 23 is disposed in the center of the constant-temperature chamber 15 from the perspective of the front surface of the upper casing 12. This vessel conveying device 23 transports the culture vessel 19 between stocker 21, the sample stand of the observation unit 22, and the conveying stand 24. When a stocker 21 is not provided, as described above, the vessel conveying device 23 is also unnecessary.

The vessel conveying device 23 includes a vertical robot 38 having a multi-joint arm, a rotary stage 35, a mini-stage 36, and an arm part 37. The rotary stage 35 is attached to the tip of the vertical robot 38 so as to be rotatable by 180° C. in the horizontal direction around a rotary shaft 35a. Therefore, the rotary stage 35 can make the arm part 37 respectively face the stocker 21, the sample stand 31, and the conveying stand 24.

In addition, the mini-stage 36 is attached so as to be slidable in the horizontal direction with respect to the rotary stage 35. The arm part 37, which grips the culture vessel 19, is attached to the mini-stage 36.

Next, an overview of the configuration of the lower casing 13 will be given. The main body portion 33 of the observation unit 22 and the control device 41 of the incubator 11 are housed inside the lower casing 13.

The control device 41 is connected to the temperature adjustment device 15a, the humidity adjustment device 15b, the observation unit 22, and the vessel conveying device 23. This control device 41 collectively controls each part of the incubator 11 in accordance with a predetermined program.

As one example, the control device 41 controls the temperature adjustment device 15a and the humidity adjustment device 15b so as to maintain the inside of the constant-temperature chamber 15 at predetermined environmental conditions. In addition, the control device 41 controls the observation unit 22 and the vessel conveying device 23 and automatically executes an observation sequence of the culture vessels 19 based on a predetermined observation schedule.

Further, based on a captured image obtained in the observation sequence, the control device 41 executes administration timing determination processing so as to output information indicating the drug administration timing corresponding to the drug type to be administered to the cells. In addition, in the administration timing determination processing, the control device 41 determines the state of the cells based on a captured image obtained in the observation sequence and outputs information indicating the current state of the cells if the state of the cells has changed.

Here, the state of the cells will be described. The state of the cells is classified into the following three states based on the degree of maturity of the cells, for example.

Induction phase
Cell growth phase
Maturation phase

The induction phase indicates a constant period in which no cell maturation or slow growth rate occurs after the culturing of the cells is initiated. Accordingly, the cell count barely changes during this induction phase. In addition, cell repair, enzyme system maintenance, and carbonic acid accumulation are performed in the induction phase.

The cell growth phase indicates a period in which cell growth is active, wherein the number of cells rapidly increasing in each unit time.

The maturation phase indicates a period after the cell growth phase. In this maturation phase, the number of cells does not change due to a balance of an increase in the number of cells due to cell maturation and a decrease in the number of cells due to cell death.

The control device 41 determines which of these three states the cells being observed have assumed based on a captured image obtained in the observation sequence and outputs information indicating the current state of the cells if the state of the cells has changed. Information indicating the state of the cells is information indicating whether the state of the cells is the induction phase, the cell maturity phase, or the stationary phase (for example, a state ID or a name expressing the state).

The configuration of the control device 41 illustrated in FIG. 3 will be now be described. This control device 41 comprises a storage part 42, an input reception part 43, an output part 45, and a control part 46.

The storage part 42 includes a nonvolatile storage medium such as a hard disk and a flash memory and a volatile storage medium such as a DRAM (Dynamic Random Access Memory) and non-volatile memory and SRAM (Static Random Access Memory). Management data related to each culture vessel 19 housed in the stocker 21, data for the entire observation image taken by the imaging device, and microscopic image data are stored in this storage part 42. This image data includes a fluorescent image taken after the cells in the culture vessel 19 are fluorescently stained. In addition, notification conditions for determining the notification timing for drug administration are stored in the storage part 42. State determination information including determination conditions for determining the state of the cells is also stored in the storage part 42. In addition, cell type coordination information described below is stored in the storage part 42. Further, programs executed by the control part 46 are stored in the storage part 42. The results of various operations performed by the control part 46 are also temporarily stored in the storage part 42. The notification conditions and state determination information will be described below.

The management data described above includes: (a) index data indicating each of the culture vessels 19; (b) the housing positions of the culture vessels 19 in the stocker 21; (c) the types and shapes (well plate, dish, flask, or the like) of the culture vessels 19 and manufacturer names; (d) the types of cells in culture in the culture vessels 19 (cell type information); (e) an observation schedule of the culture vessels 19; (f) the imaging conditions at the time of time-lapse observations (objective lens magnification, observation positions in the vessels, and the like); (g) and the types of drugs to be administered to the cells in culture in the culture vessels 19 (drug type information). In addition, for a culture vessel 19 capable of simultaneously culturing cells in a plurality of small vessels, as in the case of a well plate, management data is respectively generated for each of the small vessels.

In this embodiment, one or more cells are to be observed. In this case, cell identification information for identifying each of the plurality of cells is necessary, but cell identification information is not essential when it is unnecessary to identify the cells, such as cases in which there is only one cell to be observed. Of course, cell identification information may be inputted even if there is only one cell to be observed.

In addition, when observing cells of mutually different types, it is preferable to store cell type information indicating the cell types of the cells in the storage part 42 in association with each piece of information.

The input reception part 43 is provided with an input device such as a keyboard and a mouse. Various information such as cell type information indicating the type of cells or drug type information indicating the type of drug to be administered is inputted into the input reception part 43 by user operations.

The output part 45 is a display part such as a liquid crystal display panel and an organic EL (Electroluminescence) display panel, for example. The output part may instead be a speaker for producing audio, a vibrator for generating vibration, or a combination thereof.

The configuration of the control part 46 will be described hereinafter with reference to FIG. 3. The control part 46 comprises an image reading part 461, a detection part 462, a calculation part 463, a first determination part 464, a second determination part 465, an output control part 466, and a storage control part 467.

The control part 46 is, for example, a processor which executes various types of arithmetic processing of the control device 41. The control part may also function as each of the image reading part 461, the detection part 462, the calculation part 463, the first determination part 464, the second determination part 465, the output control part 466, and the storage control part 467 as a result of the execution of a program. In addition, some or all of these functional parts of the control part 46 may be hardware functional parts such as LSI (Large Scale Integration) or ASIC (Application Specific Integrated Circuits).

The incubator 11 might require the input of cell type information indicating the cell type (for example, a cell type ID). In addition, the cell type information may be inputted by a user who knows the cell type to be observed, or cell type information may be automatically generated and inputted by using technology for identifying the morphology or brightness of the cells to be observed and automatically determining the cell type by means of a matching technique or the like.

In this embodiment, a case in which the cell type information is inputted from a user via the input reception part 43 will be described.

In addition, the incubator 11 might require the input of drug type information indicating to the type of drug to be administered (for example, a drug type ID).

In this embodiment, a case in which the drug type information is inputted from a user via the input reception part 43 will be described.

The image reading part 461 reads image data of a microscopic image captured by the imaging device 34 and supplies the read image data to each part of the control device 41. In addition, the image reading part 461 reads image data of a microscopic image stored in the storage part 42 and supplies the image data that is read to each part of the control device 41.

The detection part 462 detects cells based on one or more microscopic image(s) taken by the imaging device 34. To detect cells, in some embodiments the detection part 462 detects cell bodies included in the microscopic image(s). In some embodiments, the detection part 462 may additionally or alternatively detect, for each cell body, a morphological feature of a cell, such as nodes, branches, or neurites of the cell in the case that the cell is a motor neuron. The detection part 462 may implement a known method for detecting cells, cell bodies, and/or morphological features. For example, the detection part 462 may implement a pattern matching technique or the like, and may analyze brightness and/or saturation of parts of one or more microscopic images. For example, the detection part 462 may implement one or more of the techniques implemented in software packages such as ImageJ available from the National Institutes of Health, CellProfiler available from the Broad Institute of Cambridge, Mass., and/or Columbus™ from PerkinElmer, Inc. of Waltham, Mass. As part of detecting cells, as discussed in further detail below, the detection part 462 may track cells over time across different microscopic images, and thus may implement one or more cell tracking techniques, including cell tracking techniques implemented in ImageJ, CellProfiler, and/or Columbus™. The detection part 462 may coordinate cell body identification information for identifying cell bodies with each of the detected cell bodies and the nodes detected for each cell body.

The calculation part 463 calculates the number of cell bodies and the number of nodes for each cell body based on the cell bodies and the nodes for each cell body detected by the detection part 462. In addition, the calculation part 463 reads cell type coordination information and cell type information of cells being observed in the current observation sequence from the storage part 42. Cell type coordination information is information in which information indicating the cell type and information indicating a predetermined number corresponding to the cell type stored in the storage part 42 in advance are coordinated. In addition, the cell type information is information included in the management data stored in the storage part 42. Further, the calculation part 463 calculates the ratio of the number of cell bodies having a number of nodes equal to or greater than a predetermined number corresponding to the cell type to the total number of cell bodies based on the cell type coordination information, the cell type information, and the calculated number of nodes for each cell body. This ratio calculated by the calculation part 463 will be called the target cell body ratio hereafter.

Next, the cell type coordination information will be described. Cell type coordination information may be stored in the form of a table T42-1. Information indicating the cell type and a predetermined number are coordinated and stored as cell type coordination information in the table 42-1. This predetermined number is a number serving as an index expressing whether cell bodies predetermined experimentally or the like for each cell type are target. As an example, the predetermined number coordinated with the cell type A is 3, and the predetermined number coordinated with the cell type B is 4. The calculation part 463 reads this cell type coordination information and cell type information of the cells being observed in the current observation sequence from the storage part 42 and generates a target cell body ratio.

The calculation part 463 may also have a configuration in which only the number of nodes for each cell body are calculated instead of a configuration in which the number of cell bodies and the number of nodes for each cell body are calculated. In this case, the calculation part 463 calculates the number of cell bodies having a number of nodes equal to or greater than a predetermined number corresponding to the cell type based on the calculated number of nodes for each cell body.

The first determination part 464 determines whether the target cell body ratio calculated by the calculation part 463 satisfies a predetermined notification condition. The predetermined notification condition is the condition that the target cell body ratio is at least 25%, but a number equal to or greater than another ratio may be used instead, and another condition based on the number of cell bodies and the number of nodes for each cell body may be used. The predetermined notification condition described here is an example of a predetermined condition.

The second determination part 465 reads state determination information stored in advance in the storage part 42. The second determination part 465 determines the state of cells being observed in the current observation sequence based on the state determination information that is read, the rate of change in the target cell body ratio calculated by the calculation part 463 during a period of time preceding the present time by a predetermined period, and the elapsed time from the start of the experiment counted by a clock part (not illustrated). The predetermined period is assumed to be 15 hours, for example, but another amount of time may be used instead. The state determination information indicates information in which information indicating the state of the cells and determination conditions for determining the state of cells based on the rate of change in the target cell body ratio calculated by the calculation part 463 during a period of time preceding the present time by a predetermined period are coordinated. Hereafter, the rate of change in the target cell body ratio calculated by the calculation part 463 during a period of time preceding the present time by a predetermined period will be simply described as the rate of change for the sake of explanatory convenience.

Next, the state determination information will be described. State determination information may be stored in the form of a table T42-2. Determination conditions and information indicating the state of the cells are coordinated and stored as state determination information in the table 42-2. In addition, the determination conditions consist of determination conditions related to the rate of change and determination conditions related to the elapsed time since the start of the experiment. Hereafter, the elapsed time since the start of the experiment will be simply described as the elapsed time for the sake of explanatory convenience.

In some embodiments, and as an example, based on the state determination information, the calculated rate of change, and the elapsed time counted by a clock part (not illustrated), the second determination part 465 determines that the state of the cells is in the induction phase if the rate of change is less than 0.65 and the elapsed time is at least 0 hours and less than 36 hours. In addition, based on the state determination information, the second determination part 465 determines that the state of the cells is the cell maturity phase if the rate of change is at least 0.65 and the elapsed time is at least 36 hours and less than 195 hours. Further, based on the state determination information, the second determination part 465 determines that the state of the cells is the stationary phase if the rate of change is less than 0.65 and the elapsed time is at least 195 hours at less than 333 hours. The state determination information may also be information in which other determination conditions and other cell states are coordinated.

If the first determination part 464 determines that the target cell body ratio satisfies the predetermined notification condition, the output control part 466 determines whether the timing for administering a drug has already been communicated. If it is determined that the timing for administering the drug has not already been communicated, the output control part 466 outputs information indicating the timing for administering the drug to the output part 45. In this example, the output control part 466 displays the information indicating the timing for administering the drug on the output part 45. On the other hand, if it is assessed that the timing for administering the drug has already been communicated, the output control part 466 enters a standby state without doing anything in particular, but it may instead perform some other kind of processing. In addition, the output control part 466 determines whether the state of the cells determined by the second determination part 465 has changed from the state of the cells determined by the second determination part 465 in the previous observation sequence and, if the state has changed, displays information indicating the current state of the cells (information indicating the state of the cells determined by the second determination part 465 in the current observation sequence) on the output part 45.

The storage control part 467 controls the writing of information outputted by each functional part of the control device 41 into the storage part 42 and the reading of information from the storage part 42.

Figure 4:
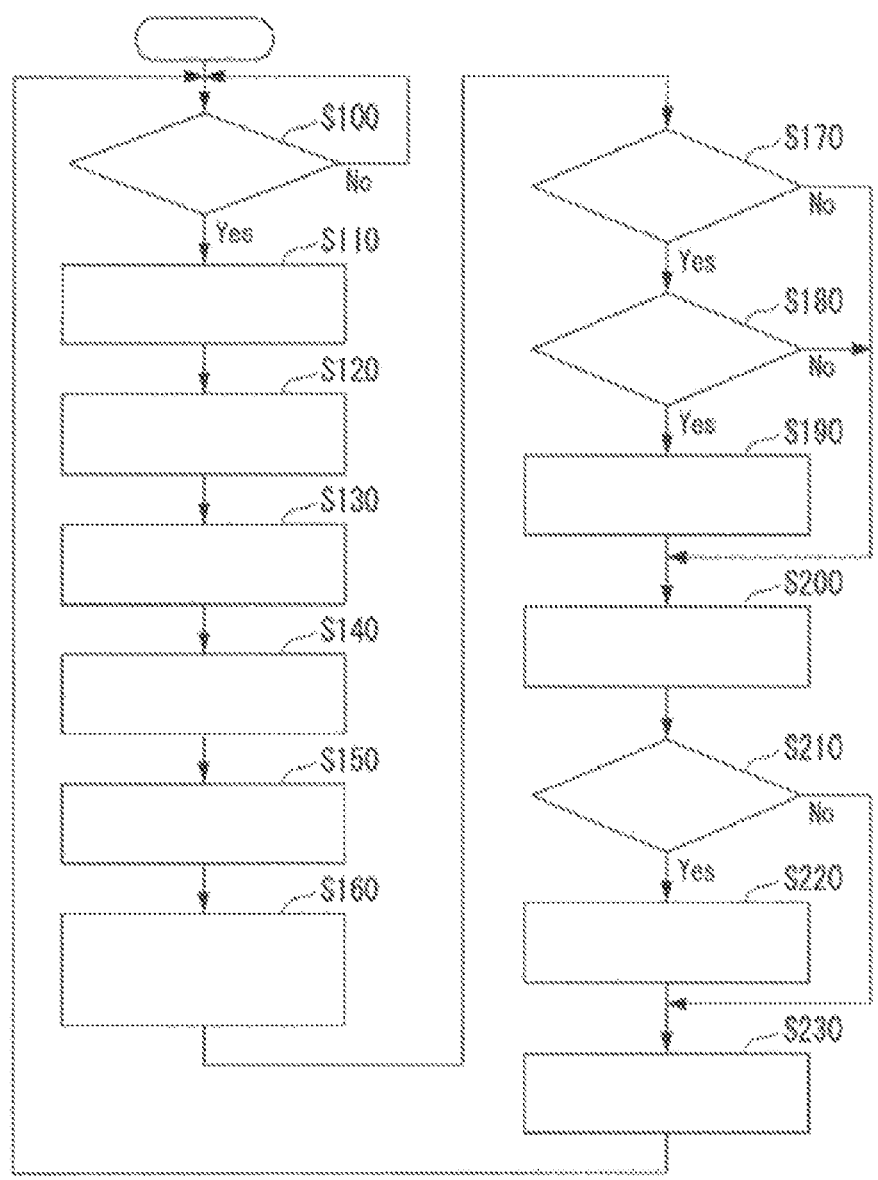
FIG. 4 is a flowchart illustrating an example of administration timing determination processing performed by the observation device provided herein.

The administration timing determination processing performed by the incubator 11 will be described hereinafter with reference to FIG. 4. FIG. 4 is a flowchart illustrating an example of the administration timing determination processing performed by the incubator 11. In this embodiment, cell type information indicating specific types of cells to be observed and drug type information indicating the types of drugs to be administered to the cells are obtained and stored in advance.

The incubator 11 conducts a time-lapse observation of the culture vessels 19 placed inside the constant-temperature chamber 15 in accordance with a registered observation schedule. A plurality of specific types of cells are cultured in the culture vessels 19. For example, cells A are cultured in the culture vessel 19A of the culture vessels 19. In addition, cells B are cultured in the culture vessel 19B of the culture vessels 19. In accordance with the observation schedule, the incubator 11 sequentially conveys the culture vessels 19A and 19B to the vertical robot 38 and the observation unit 22 and captures an image of the entire culture vessel 19 (entire observation image) and a microscopic image magnifying a portion of the culture vessel 19. The operation of the time-lapse observation of this incubator 11 will be described hereinafter.

First, the control part 46 compares the observation schedule of the management data of the storage part 42 with the current date and time, and determines whether the observation start time of the culture vessel 19 has arrived (step S100). If the observation start time has arrived (step S100—Yes), the control part 46 transitions the process to step S110. On the other hand, if the observation time of the culture vessel 19 has not arrived (step S100—No), the control part 64 waits until the time of the next observation schedule.

If the observation start time has arrived in step S100, the control part 46 instructs the vessel conveying device 23 to convey the culture vessel 19 corresponding to the observation schedule. The vessel conveying device 23 then retrieves the indicated culture vessel 19 from the stocker 21 and places the vessel on the sample stand 31 of the observation unit 22 (step S110). At the stage when the culture vessel 19 is placed on the sample stand 31, an entire observation image of the culture vessel 19 is taken by a macro-imaging camera (not illustrated) built into the stand arm 32.

In this embodiment, the observation device illustrated in FIG. 2 is a device equipped with a constant-temperature chamber for culturing the cells to be observed. Therefore, the cells imaged in step S110 are cultured in the constant-temperature chamber of the observation device. Accordingly, this step may also be initiated from the step of culturing the cells. In addition, a constant-temperature chamber is not necessarily provided inside the observation device, as in the case of this embodiment, and a constant-temperature chamber for culturing the cells may also be a separate device from the observation device.

Next, the control part 46 obtains cell type information (cell type ID) from the management data stored in the storage part 42 (step S120).

Next, the control part 46 obtains drug type information (drug type ID) from the management data stored in the storage part 42 (step S130).

Next, the image reading part 461 obtains the image data captured in step S110 (step S140). In this example, the acquisition of image data is described as a case in which data is obtained by means of fluorescence observation, but the data may instead be obtained by means of phase difference observation. When the image data is obtained by fluorescence observation, it is preferable to provide an adding device for adding a fluorescent reagent to the observation specimen prior to observation. This image data may include an image of colonies formed by cells or may be an image of single cells or a region partially including the colonies.

Next, the detection part 462 detects the cell bodies of cells contained in the image data and nodes for each cell body from the image data obtained in step S140 (step S150).

Here, the cell bodies and nodes in the captured image will be described.

As an example, the captured image contains cell bodies CB constituting cells, one or more projections PR from the cell bodies CB, nodes ND serving as joints between the projection PR and the cell bodies CB, and residual matter RM. The residual matter indicates necrotized neurites NR, for example. The detection part 462 detects the cell bodies CB and the nodes N for each cell body from the captured image using pattern matching or the like.

After the detection part 462 detects the cell bodies and the nodes for each cell body in step S150, the calculation part 463 calculates the number of cell bodies and the number of nodes for each cell body based on the cell bodies and the nodes for each cell body detected by the detection part 462 and cell body identification information coordinated with each cell body and each node. In addition, the calculation part 463 reads cell type coordination information and cell type information of cells being observed in the current observation sequence from the storage part 42. The calculation part 463 calculates the ratio of the number of cell bodies having a number of nodes equal to or greater than a predetermined number corresponding to the cell type to the total number of cell bodies as a target cell body ratio based on the cell type coordination information, the cell type information, and the calculated number of nodes for each cell body (step S160). In this example, the predetermined number corresponding to the cell type is 3, but another number may be used instead. In addition, the calculation part 463 may also be configured so as to calculate other quantities based on the number of cell bodies and the number of nodes for each cell body after calculating the number of cell bodies and the number of nodes for each cell body.

Next, the first determination part 464 determines whether the target cell body ratio calculated by the calculation part in step S160 satisfies the predetermined notification condition (step S170). In this example, the predetermined notification condition is the condition that the target cell body ratio is at least 25%, but another condition may be used instead. For example, instead of a configuration in which the calculation part 463 calculates the target cell body ratio, the predetermined notification condition may be the condition that the number of cell bodies is at least a predetermined number when calculating the number of cell bodies having a number of nodes equal to or greater than a predetermined number corresponding to the cell type. The predetermined number is 100, for example, but another number may also be used instead.

If the first determination part 464 determines that the target cell body ratio satisfies the predetermined notification condition (step S170—Yes), the output control part 466 determines whether information indicating the drug administration timing for the observed cells has already been outputted (communicated) (step S180). If it is determined that the information indicating the drug administration timing for the observed cells has not already been outputted, the output control part 466 outputs (in this example, displays) the information indicating the drug administration timing to the output part 45 (step S190), and the second determination part 465 then executes the processing of step S200. On the other hand, if the output control part 466 determines that the information indicating the drug administration timing for the observed cells has already been outputted, the second determination part 465 reads differentiation state determination information from the storage part 42. The second determination part 465 then determines the state of the cells based on the differentiation state determination information that is read, the rate of change described above, and the elapsed time described above (step S200).

On the other hand, if the first determination part 464 determines that the target cell body ratio does not satisfy the predetermined notification condition in step S170 (step S170—No), the second determination part 465 transitions to step S200 and determines the state of the cells based on the target cell body ratio calculated by the calculation part in step S160.

Next, the output control part 466 determines whether the state of the cells determined in step S200 has changed from the previously determined state of the cells (step S210). The previously determined state of the cells is assumed to be stored in a memory or the like. If it is determined that the state of the cells determined in step S200 has changed from the previously determined state of the cells (step S220—Yes), the output control part 466 outputs (in this example, displays) information indicating the current state of the cells to the output part 45 (step S220). On the other hand, if the output control part 466 determines that the state of the cells determined in step S200 has not changed from the previously determined state (step S220—No), the control part 46 instructs the vessel conveying device 23 to convey the culture vessel 19 after the completion of the observation schedule. The vessel conveying device 23 then conveys the indicated culture vessel 19 from the sample stand 31 of the observation unit 22 to a predetermined housing position of the stocker 21 (step S230). The control part 46 then ends the observation sequence and returns the process to step S100.

Thus, the sequence of events in the flow chart may be as follows:

START
OBSERVATION TIME ARRIVED?
CONVEY CULTURE VESSEL TO OBSERVATION UNIT
OBTAIN CELL TYPE INFORMATION
OBTAIN DRUG TYPE INFORMATION
READ IMAGING IMAGE
DETECT NUMBER OF CELL BODIES AND NUMBER OF NODES
CALCULATE RATIO OF CELL BODIES PRESENT WITH AT LEAST 3 NODES
NOTIFICATION CONDITIONS SATISFIED?
NOTIFIED?
OUTPUT INFORMATION INDICATING DRUG ADMINISTRATION TIMING
DETERMINE CELL STATE
CHANGE IN STATE OF CELLS?
OUTPUT INFORMATION INDICATING STATE OF CELLS
CONVEY CULTURE VESSEL TO STOCKER

As described above, the incubator 11 (observation device) of this embodiment calculates a value based on the number of cell bodies having at least a predetermined number of nodes (3 in this example) corresponding to the type of cells out of the cell bodies contained in an image (a microscopic image in this example) of cells in culture including cell bodies and nodes, determines whether the calculated value satisfies a predetermined condition (a notification condition in this example) corresponding to the drug for administration to the cells, and outputs information indicating the timing for administering the drug if it is determined that the calculated value satisfies the predetermined condition. As a result, the incubator 11 is able improve the precision of drug response evaluation.

The control device 41 may also be configured so that a plurality of microscopic images in which a plurality of points of the same culture vessel 19 (for example, 5-point observation or the entire culture vessel 19) are imaged in the same observation time range are handled as images for a single time-lapse observation.

In addition, instead of a configuration in which the incubator 11 outputs information indicating the timing for administering a drug if it is determined that a value, which is calculated by the calculation part and is based on the number of cell bodies having at least a predetermined number of nodes corresponding to the type of cells, satisfies a predetermined condition, the incubator 11 may be configured so as to determine that the cells are in a shipping period if it is determined that a value, which is calculated by the calculation part and is based on the number of cell bodies having at least a predetermined number of nodes corresponding to the type of cells, satisfies a predetermined condition, and to convey the culture vessels 19 in the observation sequence to a predetermined position for shipping with the vessel conveying device 23. This makes it possible for the incubator to align the state of the cells at the time of shipping, and as a result, the precision of drug response evaluation by a user who has purchased the shipped cells can be improved.

In addition, the various processes described above may also be performed by recording programs for executing each process of the incubator 11 (observation device) in the embodiment of the present invention on a computer-readable recording medium and then reading and executing the programs recorded on the recording medium with a computer system.

The "computer system" described here may include an OS or hardware such as peripheral equipment. In addition, "computer systems" are assumed to include home page providing environments (or display environments) when a WWW system is used.

A "computer-readable recording medium" may refer to a writable nonvolatile memory such as a flexible disk, a magneto-optical disk, a ROM, or a flash memory, a portable medium such as a CD-ROM, or a storage part such as a hard disk built into the computer system. Further, "computer-readable recording mediums" also include mediums which hold programs for a certain amount of time such as the volatile memory (for example, DRAM) and non-volatile memory inside a computer system serving as a server or a client when a program is transmitted via a network such as the internet or a communication line such as a telephone line. Computer-readable recording mediums include non-transitory media.

In addition, the program described above may be transmitted from a computer system in which the program is stored in a storage part or the like to another computer system via a transmission medium or by means of transmission waves in a transmission medium. Here, a "transmission medium" for transmitting a program refers to a medium having a function of transmitting information, as in the case of a network (communication network) such as the internet or a communication line (communication wire) such as a telephone line. In addition the program described above may be a program for realizing some of the functions described above. Further, the program may be a so-called differential file (differential program) capable of realizing the functions described above in combination with programs already recorded in the computer system.

An embodiment of the present invention was described in detail above with reference to the drawings, but the specific configuration of the present invention is not limited to this embodiment, and designs or the like within a range that does not depart from the gist of the present invention are also included in the present invention.

Cell Tracking in Culture Over Extended Periods of Time

Prior art methods for cellular responses to stimuli are disadvantaged because of the inherent variability in cell cultures, cell lines, culture parameters, and the like. This is the case when dealing with patient-specific cells such as differentiated cell populations from patient-specific pluripotent stem cells such as patient-specific iPS cells. In order to more accurately analyzed a given cell population and optionally to analyze a number of such populations, each from a different patient, concurrently, the methods provided herein allow an end user to track changes within each cell population independently from other cell populations. In this way, a plurality of analyses can be carried out simultaneously but with fine-tuned resolution as to the baseline characteristics and responses of individual populations. In addition, since readouts in these assays are typically not survival or viability, the assays may be conducted more quickly. This is particularly relevant when studying cell populations that are models of particular diseases or conditions that involve dysfunction rather than death of a target population. Even in those situations in which the disease or condition is associated with death of the target population, the assays described and provided herein may be used to identify early markers of cell death, and thus may allow for the identification of agents that may influence such markers and events upstream of cell death. In this way, the methods may be used to impact certain diseases or conditions earlier in their process or progression rather than only at later stages when changing the disease course may be far more challenging.

This disclosure therefore provides, in one aspect, a determination device that is equipped with an acquisition part that acquires the time changes in the number of cell nodes shown in time-series images of target cells, a calculation part that calculates the period of time from when the aforementioned number of nodes becomes equal to or greater than a threshold value until the aforementioned number of nodes becomes less than the aforementioned threshold value based on the time changes in the number of cell nodes acquired by the aforementioned acquisition part, and an output part that outputs information indicating the period of time calculated by the aforementioned calculation part.

This disclosure also provides, in another aspect, an observation system that is equipped with an imaging part that takes images of an area including all or a portion of the aforementioned cells and the determination device as described herein.

This disclosure also provides, in another aspect, a program to execute on a computer processing to acquire time changes in the number of cell nodes shown in time-series images captured of the aforementioned cells, processing to calculate the period of time from when the aforementioned number of nodes becomes equal to or greater than a threshold value until the aforementioned number of nodes becomes less than the aforementioned threshold value, based on the aforementioned acquired time changes in the number of cell nodes, and processing to output information indicating the aforementioned calculated period of time.

This disclosure also provides, in another aspect, a cell production method including the steps of acquiring time changes in the number of cell nodes shown in time-series images captured of the cells, calculating the period of time from when the aforementioned number of nodes becomes equal to or greater than a threshold value until the aforementioned number of nodes becomes less than the aforementioned threshold value, based on the aforementioned acquired time changes in the number of cell nodes, outputting information indicating the aforementioned calculated period of time, and operating a device to affect changes in the aforementioned cells based on the aforementioned output information.

Embodiments of the present invention will be described below. An incubator (observation device) 11 of this embodiment may calculate an index that indicates the degree of differentiation and maturation of cells having a linear structure (e.g., adherent cells that grow in a planar monolayer manner on a culture dish) and constituted by cell bodies, which have been cultured from stem cells such as induced pluripotent stem (iPS) cells or embryonic stem (ES) cells, and then outputs information related to the condition of the cells based on the calculated index. In this way, the user can accurately understand the condition of the cells quantified by the incubator (observation device) 11, and can administer the proper medical agents at appropriate timing. As a result, the precision of drug efficacy evaluation can be improved.

In addition, the incubator 11 determines what stage the states of differentiation and maturation of the cells have reached based on the calculated index and, when the determined status has changed from the previously determined status, outputs information indicating that status. In this way, oversights by the user to changes in the states of differentiation and maturation of the cells can be minimized.

The description provided below refers to neurons as an example of cells having a linear structure and constituted by cell bodies. The approach provided herein may be applied to the analysis of other cell types including other neuron types. It is to be understood that the marker being tracked may vary between cell types. Additionally, to simplify the explanation, the states of differentiation and maturation of the cells will be referred to as the differentiation state of the neurons. Also, unless specified otherwise, cell bodies and cells will not be specifically differentiated below. Namely, cell bodies and cells will be used interchangeably.

A summary of the configuration of the incubator 11 in this embodiment will be described below, referring to FIG. 2. FIG. 2 is a block diagram that illustrates an example of the configuration of the incubator 11.

This incubator 11 is a device designed to culture cells and observe their status by taking images with a microscopic camera. The incubator 11 includes an upper casing 12 and a lower casing 13. In the assembled state of the incubator 11, the upper casing 12 is installed on the lower casing 13. Further, the interior space between the upper casing 12 and lower casing 13 is vertically divided by a base plate 14.

First, a summary of the configuration of the upper casing 12 will be described. In the interior of the upper casing 12, a thermostatic chamber 15 where cells are cultured is formed. This thermostatic chamber 15 includes a temperature regulation device 15a and a humidity regulation device 15b, whereby a suitable environment for culturing cells is maintained inside the thermostatic chamber 15 (for example, an atmosphere of temperature of 37 C.° and a humidity of 90%).

A large door 16, medium door 17, and small door 18 are situated in the front of the thermostatic chamber 15. The large door 16 covers the fronts of the upper casing 12 and lower casing 13. The medium door 17 covers the front of the upper casing 12, and separates the environment in the thermostatic chamber 15 from the outside when the large door 16 is open. The small door 18 is mounted in the medium door 17, and is a door for transporting the culture containers 19 in which cells are cultured in and out. Transporting the culture containers 19 in and out through this small door 18 makes it possible to minimize environmental changes in the thermostatic chamber 15. Further, the large door 16, medium door 17, and small door 18 each maintains an airtight seal by means of gaskets P1, P2, and P3.

Additionally, a stocker 21, observation unit 22, container transport device 23, and transport stand 24 are situated in the thermostatic chamber 15. The transport stand 24 here is situated in front of the small door 18 and transports culture containers 19 in and out through the small door 18.

The stocker 21 is situated on the left side of the thermostatic chamber 15 when viewed from the front of the upper casing 12. The stocker 21 includes a plurality of shelves, wherein a plurality of culture containers 19 can be stowed in the various shelves of the stocker 21. Further, each culture container 19 accommodates cells that are to be cultured (in this example, neurons) together with culture medium. A stocker 21 is not required.

The observation unit 22 is situated on the right side of the thermostatic chamber 15, when viewed from the front of the upper casing 12. This observation unit 22 can perform time-lapse observation of the cells inside the culture containers 19.

The observation unit 22 here is situated fitted into an opening in the base plate 14 of the upper casing 12. The observation unit 22 includes a specimen stand 31, a stand arm 32, on which an illumination light source is situated hanging down above the specimen stand 31, and a main body part 33, into which an observation optical system and imaging device 34 are built. The specimen stand 31 and stand arm 32 are situated in the thermostatic chamber 15, while the main body part 33 is stowed inside the lower casing 13.

The specimen stand 31 is composed of a translucent material, and the culture containers 19 can be mounted on top thereof. This specimen stand 31 is constructed to be moveable in the horizontal direction, whereby the positions of the culture containers 19 mounted thereon can be adjusted. An LED light source 39 is also built into the stand arm 32. The imaging device 34 can acquire a microscopic image of the cells by capturing an image, via a microscope optical system, of the cells in the culture container 19, transmissively illuminated through from above the specimen stand 31 by the stand arm 32. This microscopic image is a fluorescent image captured after the cell fluorescent-stained or transfected by fluorescent protein in the culture container 19, but it may be another image, such as a phase difference image, as long as it is an image in which it is possible to detect cell bodies and nodes from the image.

The container transport device 23 is situated in the center of the thermostatic chamber when viewed from the front of the upper casing 12. This container transport device 23 transfers culture containers 19 between the stocker 21, the specimen stand 31 of the observation unit 22 and the transport stand 24. A container transport device 23 is unnecessary in cases where there is no stocker 21, as mentioned above.

The container transport device 23 includes a vertical robot 38 having an articulated arm, a rotary stage 35, a mini-stage 36, and an arm 37. The rotary stage 35 is mounted at the tip of the vertical robot 38 so that it can rotate 180° in the horizontal direction by means of a rotary shaft 35a. Therefore, the rotary stage 35 is able to move the arm 37 opposite the stocker 21, the specimen stand 31, and the transport stand 24.

Additionally, the mini-stage 36 is mounted so that it can swing in the horizontal direction relative to the rotary stage 35. The arm 37, which grasps the culture container 19, is mounted to the mini-stage 36.

Next, a summary of the configuration of the lower casing 13 will be described. The main body part 33 of the observation unit 22 and the control device 41 for the incubator 11 are accommodated in the interior of the lower casing 13.

The control device 41 is connected to each of the temperature regulation device 15a, humidity regulation device 15b, observation unit 22, and container transport device 23. This control device 41 controls the various parts of the incubator 11 according to a specified program.

As an example, the control device 41 controls the temperature regulation device 15a and humidity regulation device 15b to maintain the interior of the thermostatic chamber 15 at specified environmental conditions. The control device 41 also controls the observation unit 22 and container transport device 23 based on a specified observation schedule to automatically execute the observation sequence in a culture container 19.

Furthermore, the control device 41 executes dosing timing determination processing to output information that indicates the timing of drug dosing according to the type of medical agent administered to the neurons, based on the captured image acquired by the observation sequence. The control device 41 also determines the differentiation status of the neurons, based on the captured image acquired by the observation sequence, and when the differentiation status of the neurons has changed, outputs information that indicates the current differentiation status of the neurons.

The configuration of the control device will be described below. This control device 41 includes an input part 42A, a control part 43A, a display part 45A, and a memory part 46A.

The input part 42A includes an input device, such as a keyboard or mouse. This input part 42A is manipulated by the user to input cell type information indicating the cell type of the neurons and drug type information indicating the type of medical agents administered.

The display part 45A includes a display device, e.g., a liquid crystal display panel or organic electroluminescence (EL) display panel. Further, the display part 45A may also be a speaker that sounds a tone, a vibrator that generations vibrations, or the like, or a combination thereof.

The memory part 46A constitutes a non-volatile storage medium, such as a hard disk or flash memory, and a volatile storage medium, such as dynamic random access memory (DRAM) or static random access memory (SRAM), and the like. This memory part 46A stores management data regarding the various culture containers 19 stowed in the stocker 21, and overall observation image data and microscopic image data captured by the imaging device. This image data includes fluorescent images captured after fluorescent-staining the cells in a culture container 19. Notification parameters for determining medical agent administration timing are also stored in the memory part 46A. Determination parameters for determining differentiation status are also stored in the memory part 46A. Furthermore, programs that are executed by the control part 43A are also stored in the memory part 46A. Various computational results performed by the control part 43A are also temporarily stored in the memory part 46A.

Further, the aforementioned management data includes (a) index data to indicate individual culture containers 19, (b) the storage locations of culture containers 19 in the stocker 21, (c) the types and shapes of culture containers 19 (well plates, dishes, flasks, etc.), the name of manufacturers, (d) the types of cells being cultured in the culture containers 19 (cell type information), (e) the observation schedule in the culture container 19, (f) imaging parameters for time-lapse observation (objective lens magnification, observation points inside the container, etc.), and (g) the types of medical agents administered to the cells being cultured in the culture containers 19 (drug type information), etc. For culture containers 19 that can simultaneously culture cells in a plurality of small containers, such as well plates, respective management data are generated for each individual small container.

Further, this embodiment, is an example of observing one or more neurons as the observation targets. In this case, neuron identification information is necessary to identify each of the plurality of neurons, but neuron identification information is unnecessary in cases where there is no need to identify neurons, as in cases where only one neuron is being observed. Of course, neuron identification information can be input even when only one neuron is being observed.

Additionally, in case of observing neurons of mutually different types, it is good to store cell type information indicating the cell types of the neurons in the memory part 46A, and to relationally store the various information.

The configuration of the control part 43A will be described below. The control part 43A includes an image data acquisition part 432, detection part 434, time change calculation part 436, time change acquisition part 438, calculation part 440, and output part 442.

This control part 43A is, e.g., a processor that executes the various computational processing of the control device 41. A portion or all of these functional parts that constitute the control part 43A may be functional hardware parts, such as large scale integration (LSI) or application specific integrated circuit (ASIC).

Further, cell type information (e.g., cell type ID) indicating the cell type must be input to the incubator 11. Additionally, input of the cell type information may be input by the user, who knows the type of cells to be observed, or it is possible to automatically create and enter cell type information using technology to automatically determine the cell type by matching technology, or the like, to identify cells, e.g., by the morphology and brightness of the cells being observed.

In this embodiment, a case is described in which cell type information is input by the user via the input part 42A.

Medical agent type information (e.g., drug type ID) indicating the type of medical agent to be administered might also be input in this incubator 11.

The image data acquisition part 432 acquires image data for microscopic images captured by the imaging device 34. The image data acquisition part 432 outputs the acquired image data to the various parts of the control device 41. The image data acquisition part 432 may also acquire image data for microscopic images stored in the memory part 46A from the memory part 46A.

The relationship between the number of nodes N, which indicates the bases (connection loci) of projections (e.g., neurites and the like) protruding from a cell body, and the health status and differentiation status of the cell, will be described below. In most cases, the health status and differentiation status of a cell are evaluated as being correlated as the number of nodes N. It is also known that cells whose health status is good correlation with cell life time. Because of this, it is important to know the number of nodes N of a cell in order to understand the health status and differentiation status of the cell. The process of detecting the number of cell nodes N from the image data acquired by the image data acquisition part 432 will be described below. Further, the image data acquired by the image data acquisition part 432 may be data in which the number of cell nodes N was already detected.

The detection part 434 detects cells from image data for each image in which a plurality of images are captured in a time sequence by the imaging device 34. To detect cells, in some embodiments the detection part 434 detects cell bodies contained in a microscopic image. In some embodiments, the detection part 434 may additionally or alternatively detect, for each cell body, a morphological feature of a cell, such as the nodes, branches, or neurites of the cell in the case that the cell is a motor neuron. The detection part 434 may implement a known method for detecting cells, cell bodies, and/or morphological features. For example, the detection part 434 may implement a pattern matching technique, and may analyze brightness and/or color saturation of parts of one or more microscopic images. For example, the detection part 462 may implement one or more of the techniques implemented in software packages such as ImageJ available from the National Institutes of Health, CellProfiler available from the Broad Institute of Cambridge, Mass., and/or Columbus™ from PerkinElmer, Inc. of Waltham, Mass. As part of detecting cells, as discussed in further in this section, the detection part 462 may track cells over time across different microscopic images, and thus may implement one or more cell tracking techniques, including cell tracking techniques implemented in ImageJ, CellProfiler, and/or Columbus™. The detection part 434 may correlate cell body identification information (e.g., "cell body ID") that identifies a cell body to a detected cell body and the nodes detected on each cell body.

The time change calculation part 436 calculates the number of cell bodies based on the cell bodies detected by the detection part 434. The time change calculation part 436 also calculates the number of nodes N for each cell body, based on the nodes on each cell body detected by the detection part 434. The time change calculation part 436 executes the following processing when cell bodies are detected in each image data, and nodes are detected on each cell body, in images captured in time sequence (time-lapse) by the detection part 434. The time change calculation part 436 calculates the number of cell bodies in each of a plurality of image data and the number of nodes N on each cell body. Also, the each time point of the number of Node are calculated using "Cell Body ID".

The time change calculation part 436 also sorts the changes in the number of cell bodies, and changes in the number of nodes N on each cell body, that were calculated in the chronological order in which the image data (images) that are the source of calculations were captured. The time change calculation part 436 calculates the changes in the number of cell bodies, and changes in the number of nodes N on each cell body, in the chronological order in which the images were captured.

Namely, the time change calculation part 436 calculates the time changes in the number of cell bodies, and the time changes in the number of nodes N on each cell body, based on the time sequence image data (time-lapse images). For example, the time change calculation part 436 calculates the time changes in the number of cell bodies, and the time changes in the number of nodes N on each cell body, that were calculated as a histograph, bar graph, or differential values, etc.

The time change acquisition part 438 acquires the time changes in the number of cell bodies, and the time changes in the number of nodes N on each cell body, that were calculated by the time change calculation part 436.

The time change acquisition part 438 may also execute smoothing processing, e.g., adaptive polynomial smoothing or moving average smoothing, to smooth the time changes in the number of nodes N on each cell body that have been acquired. The time change acquisition part 438 may also smooth the time changes in the number of cell bodies that were acquired. Further, specific examples of the smoothing processing performed by the time change acquisition part 438 will be described below.

The timing calculation part 440 calculates the period in which the cells are in a healthy state based on the time changes in the number of nodes N on each cell body acquired by the time change acquisition part 438 (abbreviated "cell health period" below). The timing calculation part 440 calculates the period of time from the time that an image was captured with the number of nodes N equal to or greater than a threshold value NTh until the time that an image was captured with the number of nodes N below the threshold value NTh as the cell health period.

The threshold value NTh will be described here. The threshold value NTh is preset to the number of nodes N (e.g., 3) on a cell at which the cell can be evaluated as being healthy, based on the correlation between the number N of nodes on a cell and the healthy state of the cell, discussed above.

This makes it possible for the control device 41 to determine the health status of a cell by calculating the number of nodes N in a cell, and as a result the longevity of the cell can be estimated.

The timing calculation part 440 may also calculate the number Ca of cell bodies in which the number of nodes N per each cell body is equal to or greater than the threshold value NTh, and the total number CT of cell bodies, from all the image data. In this case, the timing calculation part 440 may also calculate the percentage (Ca/CT) of the number Ca of cell bodies in which the number of nodes N per each cell body is equal to or greater than the threshold value NTh and the total number CT of cell bodies that were calculated. This percentage (Ca/CT) calculated by the timing calculation part 440 will be referred to and described below as the healthy cell body percentage.

The timing calculation part 440 may also calculate the cell health period described above when the healthy cell body percentage is equal to or greater than a specified percentage (e.g., 50%). Further, the timing calculation part 440 may also have a portion or all of the functions of the time change calculation part 436 and time change acquisition part 438 described above.

The output part 442 outputs information indicating the calculation results calculated by the timing calculation part 440 to the display part 45A. The output part 442 may also output information indicating the calculation results of the timing calculation part 440 to external equipment via a hardware interface. The user may determine the timing at which medical agents are administered to the culture containers 19 based on the information displayed by the display part 45A. The user may also determine the type of medical agents administered to the culture containers 19 based on the information displayed by the display part 45A. In this way, the user can electively cause cells to differentiate.

The cell bodies and nodes in the captured images will be described here. The following is an exemplary description of a neuron in a captured image. The capture image contains a cell body CB that constitutes the neuron, one or more neurites NR protruding from a cell body CB, nodes ND that are the bases of the neurites NR from the cell body CB, and residual material RM. Residual material RM indicates, e.g., a necrotic neurite NR. The detection part 434 uses pattern matching and the like to detect cell bodes CB and the nodes ND on each cell body from a captured image.

The specific configuration of each functional part will be described below. First, the specific configuration of the detection part 434 will be described. The disclosure contemplates an analysis being conducted using images of a cultured neuron captured in a time series. As described herein, a specified medical agent may be administered at time te to the cell body CB of the neuron captured at time t0, for example.

The specified medical agent affects treatment to cause a change in the cell and, e.g., is a toxic compounds, or a growth promoter that promotes cell growth or compounds for cell differentiation. The specified medical agent also may be, e.g., something that artificially introduces an agonist, virus, or the like to a cell. Further, information indicating the specific medical agent (drug type information) is input in advance by the user via the input part 42A.

As a result of the specified medical agent being administered, e.g., the cell body CB of the neuron forms 3 neurites at time t1. Namely, the cell body CB of the neuron differentiates. In this case, the detection part 434 detects 3 nodes ND1 through ND3. In addition, the cell body CB of the neuron forms one more neurite at time t2, after more time has passed from time t1, forming a total of 4 neurites. In this case, the detection part 434 detects 4 nodes ND1 through ND4.

The smoothing processing of the time change acquisition part 438 and the cell health period calculation processing of the timing calculation part 440 will be described next. Consider a diagram that illustrates the number of nodes N in a time series. The vertical axis is, e.g., the number of nodes N, and the horizontal axis is, e.g., the observation time t (unit is (s)). The various times t0, t1, t2, te, each correspond to a particular time, as discussed above. In addition, LN1 is a curve that represents the number of nodes N calculated by the time change acquisition part 438. Additionally, LN2 is a curve in which the time change acquisition part 438 has performed smoothing processing on LN1.

The timing calculation part 440 determines, e.g., whether the smoothed value (number of nodes N) of LN2 is equal to or greater than a threshold value NTh. The unsmoothed number of nodes N (LN1) is a positive integer. Therefore, when the timing calculation part 440 determines whether the natural number that the value for LN2 can be is equal to or greater than the threshold value NTh, it is acceptable to perform quantization to the value of LN2. When the threshold value NTh is, e.g., 3, the timing calculation part 440 determines that a value for LN2 of not less than 2.5 as being equal to or greater than 3.

In the illustrated example, the timing calculation part 440 determines that, e.g., the value for LN2 is equal to or greater than the threshold value NTh at time t1, and determines that the value for LN2 has become less than the threshold value NTh at time t2. In this case, the timing calculation part 440 calculates the period of time from time t1 to time t2 as the cell health period.

The timing calculation part 440 may also calculate the period of time from time te to time t2, which is the timing at which the specified medical agent is to be administered. In this case, the time te is set, e.g., to the time at which the value for LN1 is equal to or greater than the threshold value NTh, and a specified time (e.g., 3 hours) has lapsed.

The timing calculation part 440 also may execute the following processing based on the healthy cell body percentage Ca/CT. The timing calculation part 440, e.g., calculates the period of time from the time when the healthy cell body percentage Ca/CT is equal to or greater than a specified percentage until the time when it falls below the specified percentage as the cell health period. In this way, errors due to variations in cell differentiation status (growth) can be minimized.

The various information associated with a cell body ID may be illustrated as an output. The cell body ID is stored in the memory part 46A correlated to information such as, e.g., the cell health period calculated by the timing calculation part 440, the total number CT of cell bodies, the number of cell bodies Ca for which the number of nodes N is equal to or greater than the threshold value NTh, the healthy cell body percentage Ca/CT, management data, and the like. The cell body ID is, e.g., a symbol that is an amalgamation of information such as the date of observation, cell line, cell derivation source, and the like.

Information indicating the cell health period may be output to a display unit 45A. The output part 442 performs control so that, e.g., images that show the cell health period for each cell body ID are output to the display part 45A. Further, the output part 442 may also perform control to also output information, such as the number of cell bodies Ca and healthy cell body percentage Ca/CT, to the display part 45A in combination with the cell health period. The output part 442 may also perform control to output numeric data indicating the cell health period to the display part 45A, and control to output information that combines image and numeric data to the display part 45A.

Figure 5:
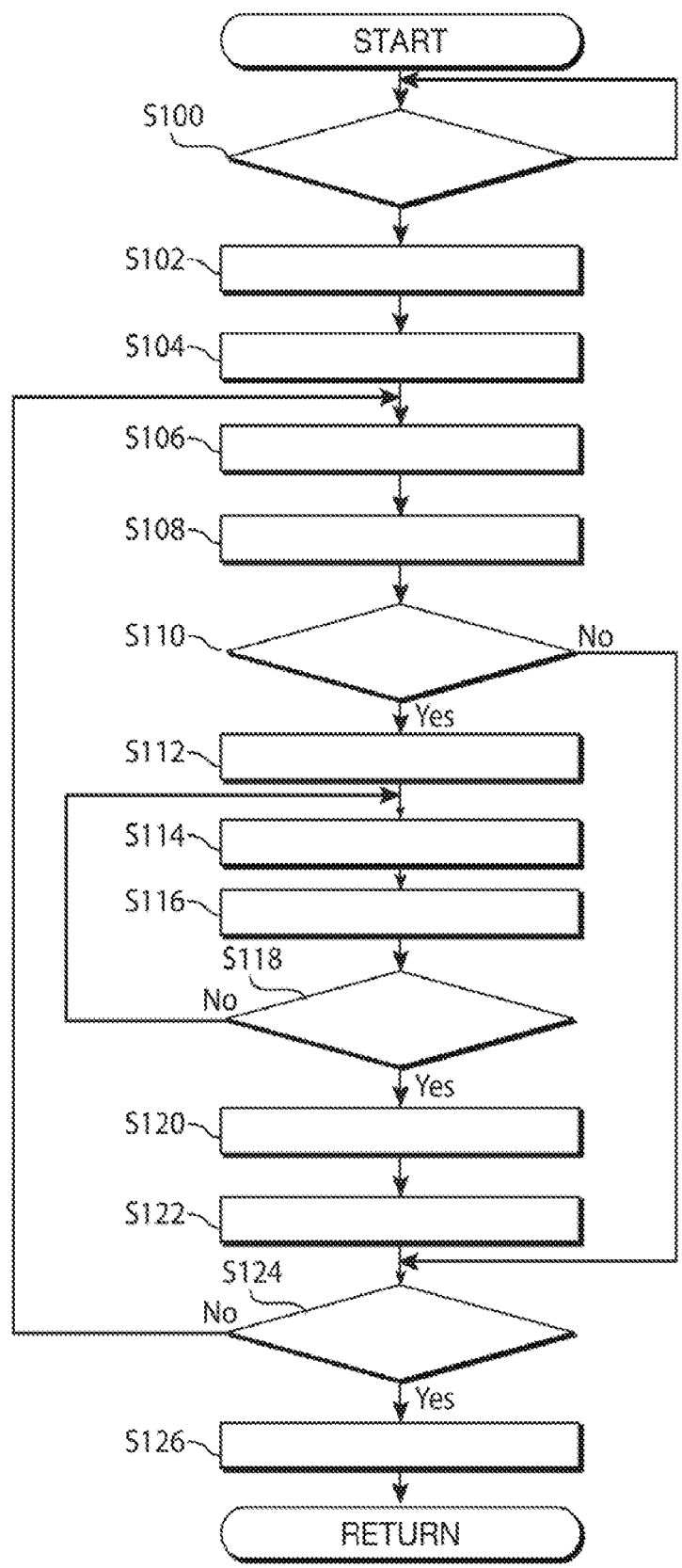
FIG. 5 is a flow chart that depicts an example of processing by an incubator 11 equipped with a control device 41.

Description of Incubator 11 Processing Sequence:

The processing sequence of an incubator 11, equipped with a control device 41, will be described below, referring to FIG. 5. FIG. 5 is a flow chart that illustrates an example of processing by an incubator 11 equipped with a control device 41. In this embodiment, information indicating various parameters for observation (abbreviated "observation parameters" below), such as cell type information indicating the specific type of neurons that are the object of said observation and drug type information indicating the type of medical agents to be administered to the neurons, has been acquired and stored in advance.

The incubator 11 performs time-lapse observation according to a registered observation schedule of culture containers 19 that have been transported into the thermostatic chamber 15. A plurality of specific types of neurons have been cultured in these culture containers 19. For example, neuron A is cultured in a culture container 19A of the culture containers 19. Additionally, a neuron B is cultured in a culture container 19B of the culture containers 19. The incubator 11 sequentially transports the culture container 19A and culture container 19B into the observation unit 22 on the vertical robot 38, and acquires an overall image of the culture container 19 (overall observation image) and a microscopic image that enlarges a portion of the culture container 19, according to the observation schedule. A time-lapse observation operation of this incubator 11 will be described below.

First, the control part 43A compares the observation schedule in the management data in the memory part 46A with the current date and time, and determines whether to start observation of the culture container 19 (step S100). If observation is started (step S100—YES), the control part 43A moves processing to step S110. On the other hand, if observation of the culture container 19 is not started (step S100—NO), then the control part 43A stands by until the next time in the observation schedule.

When observation is started at step S100, the control part 43A instructs the container transport device 23 to transport the culture container 19 according to the observation schedule. The container transport device 23 then transports the indicated culture container 19 from the stocker 21 and places it on the specimen stand 31 of the observation unit 22 (step S102). Further, at the stage where the culture container 19 has been placed on the specimen stand 31, an overall observation image of the culture container 19 is captured by the macro-photographic camera (not illustrated) that has been built into the stand arm 32.

In this embodiment, the observation device illustrated in FIG. 2 are devices equipped with a thermostatic chamber in which neurons that are to be observed are cultured. Consequently, the neurons being captured at step S102 have been cultured in the thermostatic chamber of the observation device. Therefore, it also possible to begin this step from a step where the neurons are cultured. Additionally, the thermostatic chamber also may not be built into the observation device, as in this embodiment, but may also be a device in which the thermostatic chamber for culturing neurons is a separate device from the observation device.

Next, the control part 43A acquires the observation parameters from the management data stored in the memory part 46A (step S104).

The image data acquisition part 432 then acquires the image data captured in step S102 (step S106). As acquisition of image data, a case of acquisition by fluorescent observation will be described in this example, but it may instead be acquired by phase difference observation, confocal observation, super-resolution observation, and the like. In cases where image data is acquired by fluorescent observation, it is preferable to provide an adding device that adds a fluorescence reagent or transfect Fluorescent protein to the observation specimen before observation. This image data may also include images of colonies formed by the neurons, as well as images of individual neurons or partial regions of the material of said colony.

Next, the detection part 434 detects the cell bodies of neurons and nodes on each cell body contained in this image data from the image data acquired in step S106. At step S150, after the detection part 434 has detected cell bodies and nodes per cell body, the time change calculation part 436 respectively calculates the time change in the number of cell bodies and the time change in the number of nodes N per cell body based on the cell bodies and nodes per cell body detected by the detection part 434, and on cell body identification information that correlates the various cell bodies and the various nodes. Next, the time change acquisition part 438 acquires the time change in the number of cell bodies and the time change in the number of nodes N per cell body that were calculated by the time change calculation part 436 (step S108).

Next, the timing calculation part 440 determines whether the number of nodes N per cell body is equal to or greater than the threshold value NTh (step S110). When the number of nodes N per cell body is less than the threshold value NTh (step S110—NO), the control part 43A executes the processing in step S122, described below. When the number of nodes N per cell body is equal to or greater than the threshold value NTh (step S110—YES), the timing calculation part 440 starts a clock from the time at which the number of nodes N became equal to or greater than the threshold value NTh. Next, the image data acquisition part 432 acquires the image data for the image captured at the next time after the time at which the image data acquired by the processing at step S106 was captured (step S114).

Next, the detection part 434 detects the cell bodies of neurons and the nodes for each cell body contained in this image data from the image data acquired at step S114. After the processing at step S150, the time change calculation part 436 respectively calculates the time change in the number of cell bodies and the time change in the number of nodes N per cell body based on the cell bodies and nodes per cell body detected by the detection part 434, and on cell body identification information that correlates the various cell bodies and the various nodes. Next, the time change acquisition part 438 acquires the time change in the number of cell bodies and the time change in the number of nodes N per cell body that were calculated by the time change calculation part 436 (step S116). Next, the timing calculation part 440 determines whether the number of nodes N per cell body is less than the threshold value NTh (step S118). If the number of nodes N per cell body is not less than the threshold value NTh (step S118—NO), the control part 43A executes the processing in step S114. The timing calculation part 440 stops the clock when the number of nodes N per cell body is less than the threshold value NTh (step S118—YES) (step S120). Next, the timing calculation part 440 calculates the period of time from the time that the clock was started until the time that the clock was stopped as the cell health period. The output part 442 outputs information indicating the cell health period calculated by the timing calculation part 440 to the display part 45A (step S122).

Next, the control part 43A compares the observation schedule in the management data in the memory part 46A with the current date and time, and determines whether to end observation of the culture container 19 (step S124). If observation of the culture container 19 is not ended (step S124—NO), the control part 43A returns processing to step S106. If observation of the culture container 19 is ended (step S124—YES), the control part 43A instructs the container transport device 23 to transport the culture container 19 after the observation schedule has ended. The container transport device 23 then transports the indicated culture container 19 from the specimen stand 31 on the observation unit 22 to a specified storage location in the stocker 21 (step S126). The control unit 43A then ends the observation sequence and returns processing to step S100.

Thus, a sequence of events in the flow chart of FIG. 5 may be as follows:
START OBSERVATION?
TRANSPORT CULTURE CONTAINER TO OBSERVATION UNIT
ACQUIRE OBSERVATION PARAMETERS
ACQUIRE IMAGE DATA
ACQUIRE TIME CHANGES IN CELL BODY COUNT AND NODE COUNT N
IS NODE COUNT N≥THRESHOLD VALUE Nth?
ACQUIRE IMAGE DATA
ACQUIRE TIME CHANGES IN CELL BODY COUNT AND NODE COUNT N
IS NODE COUNT N≥THRESHOLD VALUE Nth?
TERMINATE CLOCKING OUTPUT INFORMATION INDICATING CELL HEALTH PERIOD
END OBSERVATION?
TRANSPORT CULTURE CONTAINER TO STOCKER As described above, the incubator 11 (observation device) in this embodiment acquires time changes in the number of nodes N in cells shown by time-series images captured of the cells, calculates a cell health period that indicates the period of time from when the number of nodes N becomes equal to or greater than a threshold value NTh until the number of nodes N becomes less than the threshold value NTh based on the time changes in the number of nodes in the cells that have been acquired, and outputs information based on the cell health period that has been calculated, and thereby shortens the determination time and improves the determination accuracy in drug evaluations.

The incubator 11 (observation device) in this embodiment also can minimize the influence of noise by smoothing the number of nodes N based on the time changes in the number of nodes N in the cells shown in the time-series images. As a result, the incubator 11 (observation device) can make the correlation between the number of nodes N and the cell status more clear, improving the determination accuracy.

Other embodiment examples (modification examples) are described below.

The control device 41 may also be constituted to handle a plurality of microscopic images that capture a plurality of points in the same culture container 19 (e.g., observations of points or the culture container 19 overall) in the same observation time band as the images of a single pass worth of time-lapse observation.

Additionally, programs to execute the various processing of the incubator 11 (observation device) in the embodiment of the present invention may be recorded on a recording medium that can be read by a computer, and then the various processing described above can be executed by loading the programs recorded on said recording medium to a computer system and executing the programs.

Further, the "computer system" referred to here may also include an OS and hardware, such as peripheral equipment. In addition, the "computer system" may also include the environment to present a home page (or display environment) in cases where a WWW system is employed.

The "recording medium that can be read by a computer" may refer to a writeable non-volatile memory, such as floppy disk, magneto-optical disk, ROM, or flash memory, portable medium, such as CD-ROM, or memory device, such as a hard disk, built into the computer system. Furthermore, the "recording medium that can be read by a computer" includes those that can hold the program for a set time, such as volatile memory (e.g., DRAM) internal to a computer system including a server or client in cases where the program is transmitted via a network, such as the Internet, or communication lines, such as telephone circuits. Computer-readable recording mediums include non-transitory media.

Additionally, the aforementioned program may also be transferred from the computer system where the program is stored on a memory device or the like to another computer system via a transmission medium or by transmission waves in the transmission medium. The "transmission medium" that transmits the program here refers to a medium with the function of transmitting information, such as a network (communication network), such as the Internet, or a communication circuit (communication line), such as a telephone circuit. Additionally, the above program may also be one for realizing some of the functions described above. Furthermore, the program can be a so-called difference file (difference program), which can be realized in combination with a program already recorded on the computer system.

The foregoing was but one embodiment of this disclosure. The specific constitution thereof is not limited to the embodiment, and includes designs and the like within a scope that does not deviate from the gist of this disclosure.

Reference Signs List is as follows:
11 Incubator
12 Upper casing
13 Lower casing
15 Constant-temperature chamber/thermostatic chamber
15a Temperature adjustment device/temperature regulation device
15b Humidity adjustment device/regulation device
16 Large door
17 Middle door
18 Small door
19 Culture vessel/culture container
21 Stocker
22 Observation unit
23 Vessel conveying device/container transport device
24 Conveying stand/transport stand
31 Sample stand/specimen stand
32 Stand arm
33 Main body portion/main body part
34 Imaging device
35 Rotary stage
35a Rotary shaft
36 Mini-stage
37 Arm part
38 Vertical robot
39 LED light source
41 Control device
42 Storage part
42A Input part
43 Input reception part
43A Control unit/control part
45 Output part
45A Display unit/display part
46 Control part
46A Memory part
432 Image acquisition part
434 Detection part
436 Time change calculation part
438 Time change acquisition part
440 Timing calculation part
442 Output part
461 Image reading part
462 Detection part
463 Calculation part
464 First determination part
465 Second determination part
466 Output control part
467 Storage control part Examples have been described above of functionality that may be implemented by an incubator (e.g., incubator 11 of FIG. 1B). It should be appreciated, however, that embodiments are not limited to implementing all or any of the functionality described above in the illustrative incubator described above or any other particular device. For example, functionality described above as being implemented by a control part of a control device of an incubator, including functionality described in examples above as being implemented by one or more detection parts, calculation parts, acquisition parts, determination parts, and output parts (which may be individually and collectively referred to below as "analysis" functionality), may not be implemented by an incubator in some embodiments. In other embodiments, for example, such analysis functionality may instead be implemented by one or more computing devices, which may be disposed near or remote from the incubator.

In some embodiments, one or more computing device(s) may communicate with the incubator over one or more wired and/or wireless communication networks, including personal area networks, local area networks, wide area networks, and/or the Internet, to receive data collected by the incubator, such as image data obtained by the incubator as described above. Though, in other embodiments, data may be communicated to the computing device(s) in other ways, as embodiments are not limited to exchanging data in any particular manner. In embodiments in which analysis functionality may be implemented by one or more computing devices, any suitable computing devices may be used, as embodiments are not limited in this respect. In some embodiments, for example, the analysis functionality may be implemented by one or more desktop and/or laptop personal computers, one or more tablet computers, one or more mobile phones, one or more servers which may be, for example, arranged as a distributed network of servers that share processing resources, or any other suitable computing device.

As a specific example of such an embodiment, one or more computing devices (e.g., servers) may implement functionality described above as being performed by parts of the control parts of the exemplary incubators. For example, functionality for reading and analyzing image data and outputting a result of the analyzing may be implemented by the one or more computing devices. As a specific example, functionality for determining a state of cells and/or a timing at which to administer a drug may be implemented by the one or more computing devices. In response to receiving image data, such as image data generated by an incubator or other source of microscopic images, the image data may be analyzed in accordance with the functionality described above to, for example, determine a state of cells and/or a time at which to administer a drug. A result of the analysis may be output for presentation to a user, including by being output for transmission across one or more networks, such as a local network or the Internet.

In embodiments that implement analysis functionality on one or more computing to devices, information that is described above as being output via a user interface may be output via any suitable user interface of any suitable computing device, including a user interface of the same computing device(s) as are performing the analysis or a different computing device. For example, in some embodiments, a computing device that performs some or all of the analysis functionality may transmit a result of that analysis to another computing device.

Further, it should be appreciated that embodiments are not implemented to applying the analysis functionality to image data or other data obtained by or derived from an incubator or a device that is implemented in the manner of the incubator described above. Rather the analysis functionality may be performed on data, including image data, obtained from any suitable device.

The present invention is further illustrated by the following Example, which in no way should be construed as further limiting.

The entire contents of all of the references (including literature references, issued patents, published patent applications, and co pending patent applications) cited throughout this application are hereby expressly incorporated by reference, in particular for the teachings that are referenced herein.

EXAMPLE

Example 1

Long-term live cell imaging of stem cell-derived neurons has the potential to be a novel platform for drug discovery in neurodegenerative disease which has not been successfully implemented. The detailed long-term live analysis of stem cell-derived motor neurons (MNs) using the Nikon BioStation CT has been conducted. Imaging analysis algorithms accurately tracked key attributes such as cell body size, neurite number and neurite length. The imaging tools were used to study MNs subjected to two different stressors: neurotrophic factor (TF) withdrawal at early and late times and treatment with the proteasome inhibitor MG132. A new, morphological predictor for cell death that involves measurement of neuritic changes was defined. This analysis algorithm determines the "healthy time (HT)" for each MN, and this metric reveals the kinetics of survival responses that are not apparent with endpoint analysis. Quantifying disrupted neurites as an index of disease onset is advantageous since these changes occur early in the death process. These studies indicate that live cell imaging is a useful platform for characterizing stem cell-derived populations and may be a novel approach to identifying new therapeutic molecules.

In order to overcome the limitations in endpoint immunostaining analysis, a live cell imaging platform was created to characterize survival responses of in vitro-derived neurons and to identify morphological characteristics that discern survival of neurons that precede cell death and which can be tracked over time.

Figure 6A:
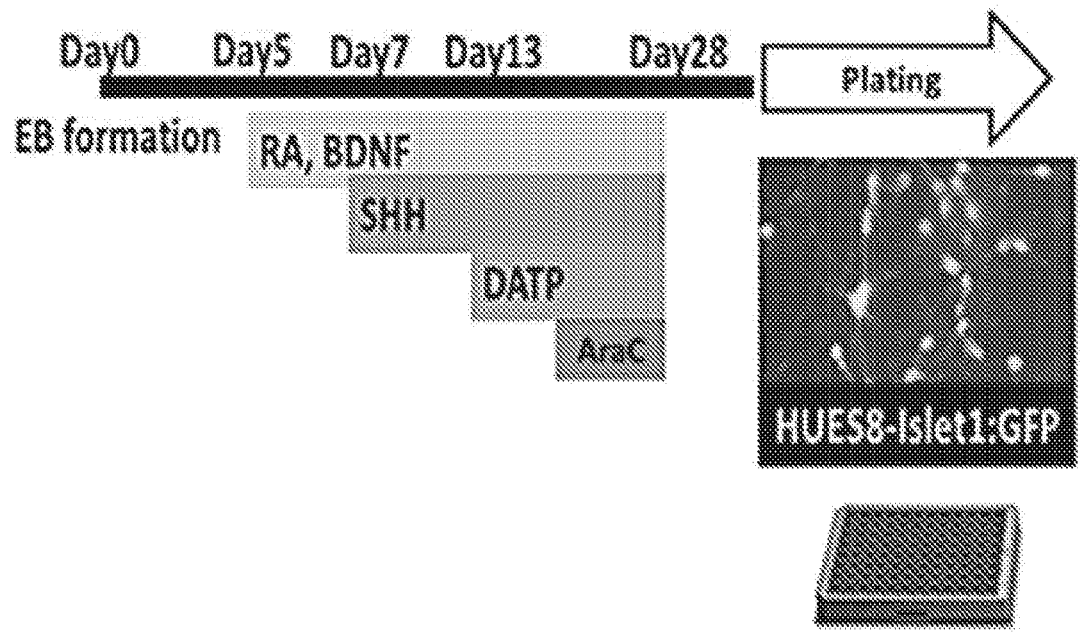
FIGS. 6A-6E show a schematic depicting the process of extended time-lapse imaging technology.
Figure 6B:
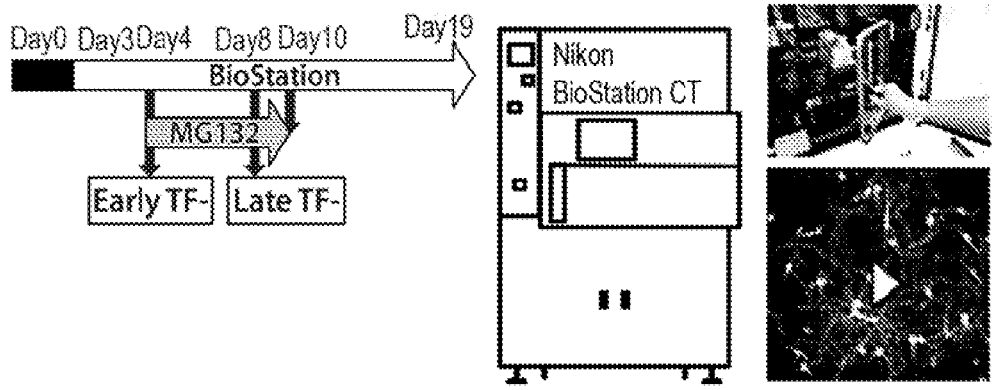
Figure 6C:
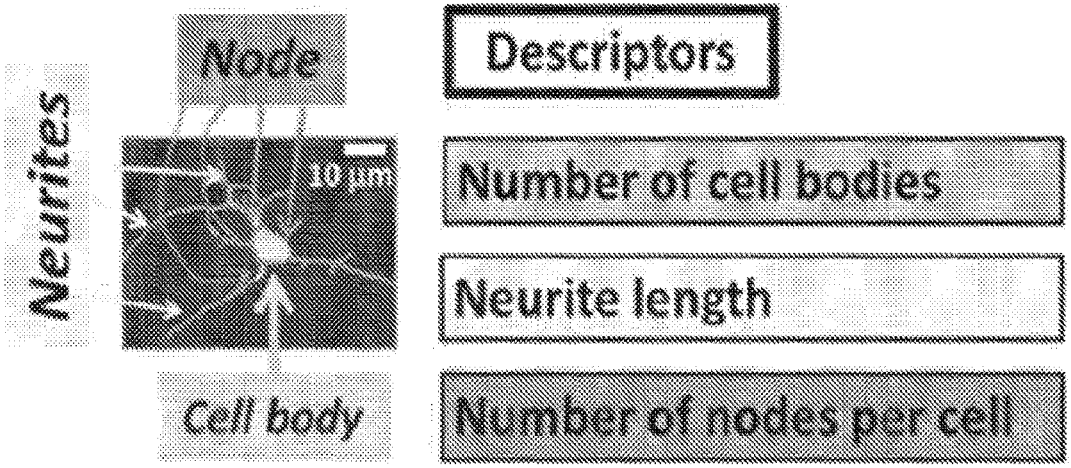
Figure 6D:
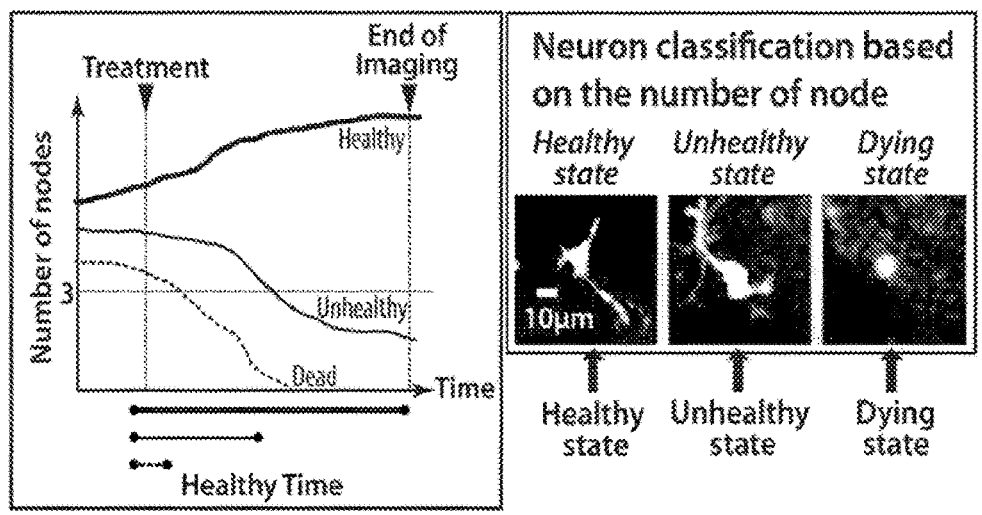
Figure 6E:
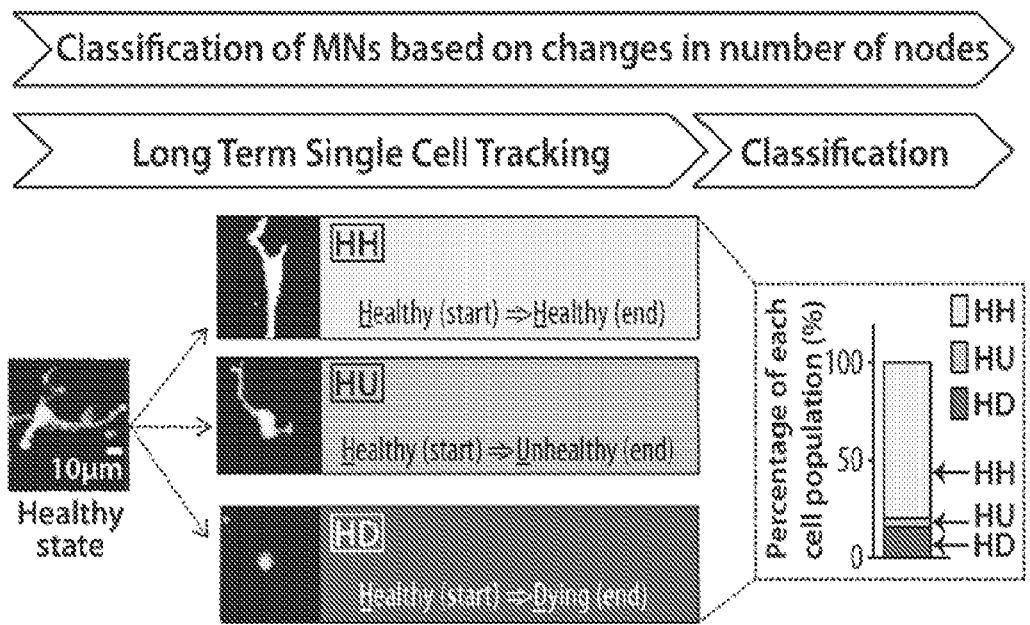

The process of live cell extended time-lapse imaging is shown in FIGS. 6A-6E. Motor neurons derived from human embryonic stem cells (hESCs) were grown for 28 days. The differentiated progeny were then plated and subjected to the trophic factor (TF) withdrawal test (either on Day 4, the early time point, or on Day 8, the late time point) or the MG 132 (proteasome inhibitor) test (from Day 4 to Day 10). The end point of the analysis was Day 19 (FIG. 6A). The cells were monitored using live imaging on the BioStation CT (FIG. 6B). Video time lapse phenotypic analysis was performed, with respect to three descriptors: the number of cell bodies, the neurite length, and the number of nodes per cell (FIG. 6C). Neurons were then classified by the number of nodes: "healthy" neurons had more than three nodes, whereas unhealthy or dying neurons had progressively fewer nodes. In this example, a healthy time assay was performed to measure the length of time any given neuron was "healthy" or had more than three nodes (FIG. 6D). The motor neurons were further classified based on changes in the number of nodes through long term single cell tracking. Starting from a healthy (H) state, the neuron had three potential outcomes: healthy end (denoted HH), unhealthy end (denoted HU), or dying end (denoted HD) (FIG. 6E). As shown in the lower right graph of FIG. 6E, the majority of motor neurons that began in a healthy state ended the protocol in a healthy state (denoted HH).

Figure 7:
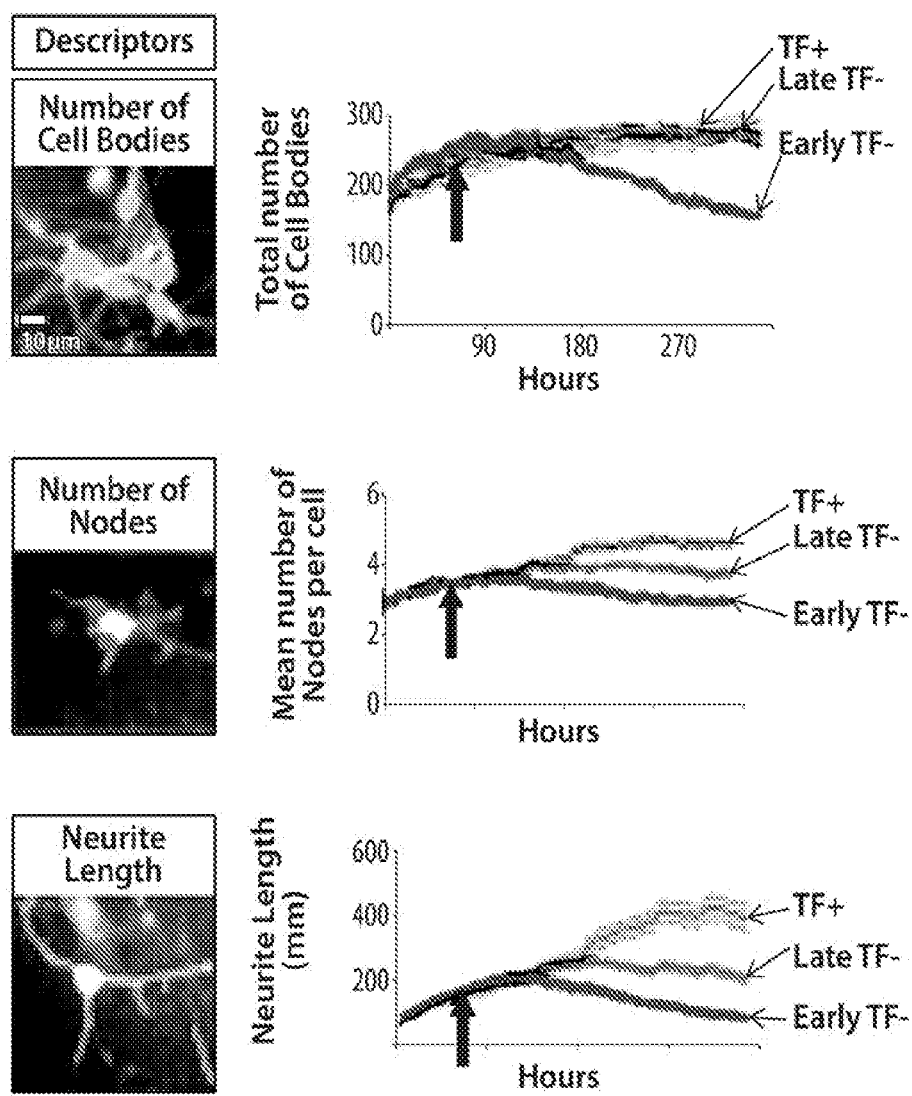
FIG. 7 illustrates results of an experiment tracking the effect of a stimulus on motor neurons using the methods provided herein. The experimental data indicate that early trophic factor (TF) withdrawal has a more substantial effect on motor neurons than late TF withdrawal. The top panel is a time plot of motor neuron (MN) cell body number over two weeks of imaging. The middle panel is a time plot of average number of nodes per MN. The lower panel is a time plot of total neurite length. The arrows indicate TF withdrawal.
Figure 8:
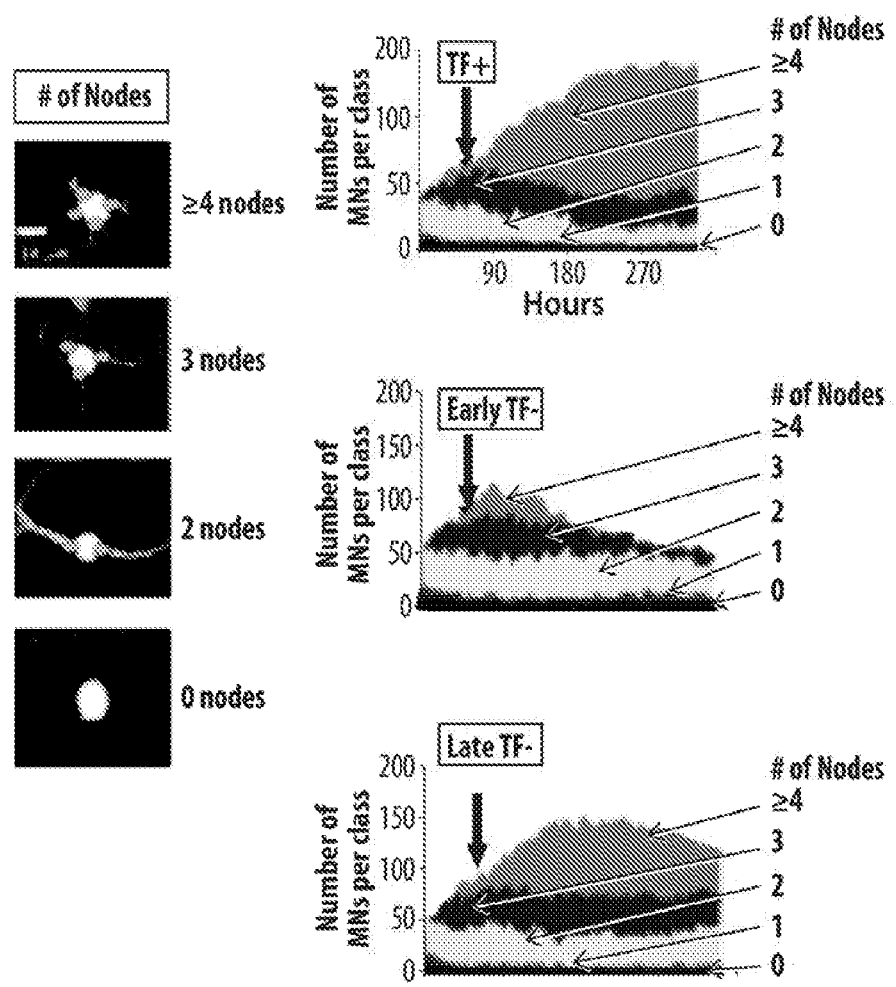
FIG. 8 corresponds with the data in the middle panel of FIG. 7. Following early TF-, there is a rapid loss of MN with 4 or more nodes. In late TF-, there is a delayed and more subtle change in the population of MN with 4 or more nodes. The arrows indicate TF withdrawal.
Figure 9:
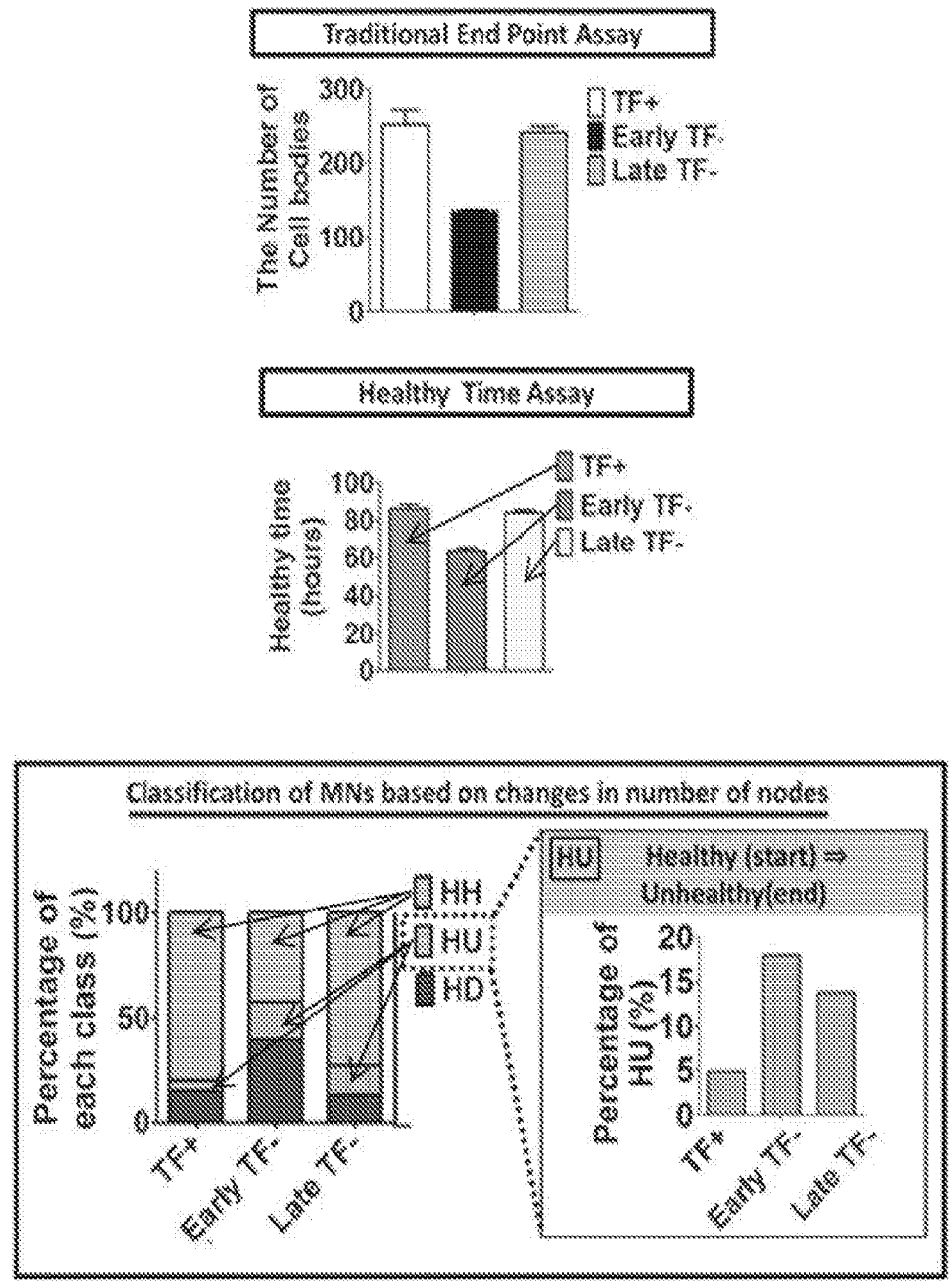
FIG. 9 illustrates that the slow death response of late TF- is apparent with live cell analysis, but not evident by endpoint analysis. The top panel shows that with endpoint analysis, there is no significant death following late TF-. The middle panel shows healthy time measures the time during which MNs have 3 or more nodes. The lower left panel presents the categorization outcome of neurons with 3 or more nodes, which show the changes in distribution of healthy and unhealthy MN. The lower right panel shows the HU population is increased following early and late TF-.

Tracking number of nodes and neurite length of motor neurons (MNs) is more informative than the number of cell bodies, as shown in FIG. 7. Live single cell tracking of MNs by the number of nodes reveals that changes in node number are an early event following cell stress, as illustrated in FIG. 8. Classification of MNs based on changes in number of nodes provides more detailed survival information than traditional endpoint studies, as demonstrated in FIG. 9.

In conclusion, the methods described herein can be used to accurately track individual motor neurons derived from ES cells for up to 2 weeks in either 48 well or 96 well plates. Characterizing motor neurons by changes in node number captures more detailed population information than traditional measurements. In vitro-derived MNs have a differential response to TF withdrawal, depending on the time at which the stress is given. Live single cell imaging has the potential to add new dimensions to characterizing human diseases mechanisms using iPS cells.

Example 2

The disclosure provides and demonstrates processes for generating differentiated cells such as motor neurons from pluripotent stem cells such as embryonic stem cell lines and patient specific iPS cells and assessing the response of such differentiated cells to stress-inducing stimuli and stress-recovery stimuli. As an example, a stress-inducing stimulus is withdrawal of trophic factors from a motor neuron cell culture. As an example, a stress-recovery stimulus is addition of trophic factors into a motor neuron cell culture. The processes and methods provided herein can be used to assess the effect of such stimuli on the population of motor neurons as well as on individual motor neurons. The motor neurons can be assessed according to for example number of cell bodies in the culture, number of nodes per cell, neurite length, distribution of cells having 0, 1, 2, 3, 4 or more nodes, time during which an individual neuron has 3 or more nodes (referred to as "healthy time" in some instances), etc.

Figure 1B:
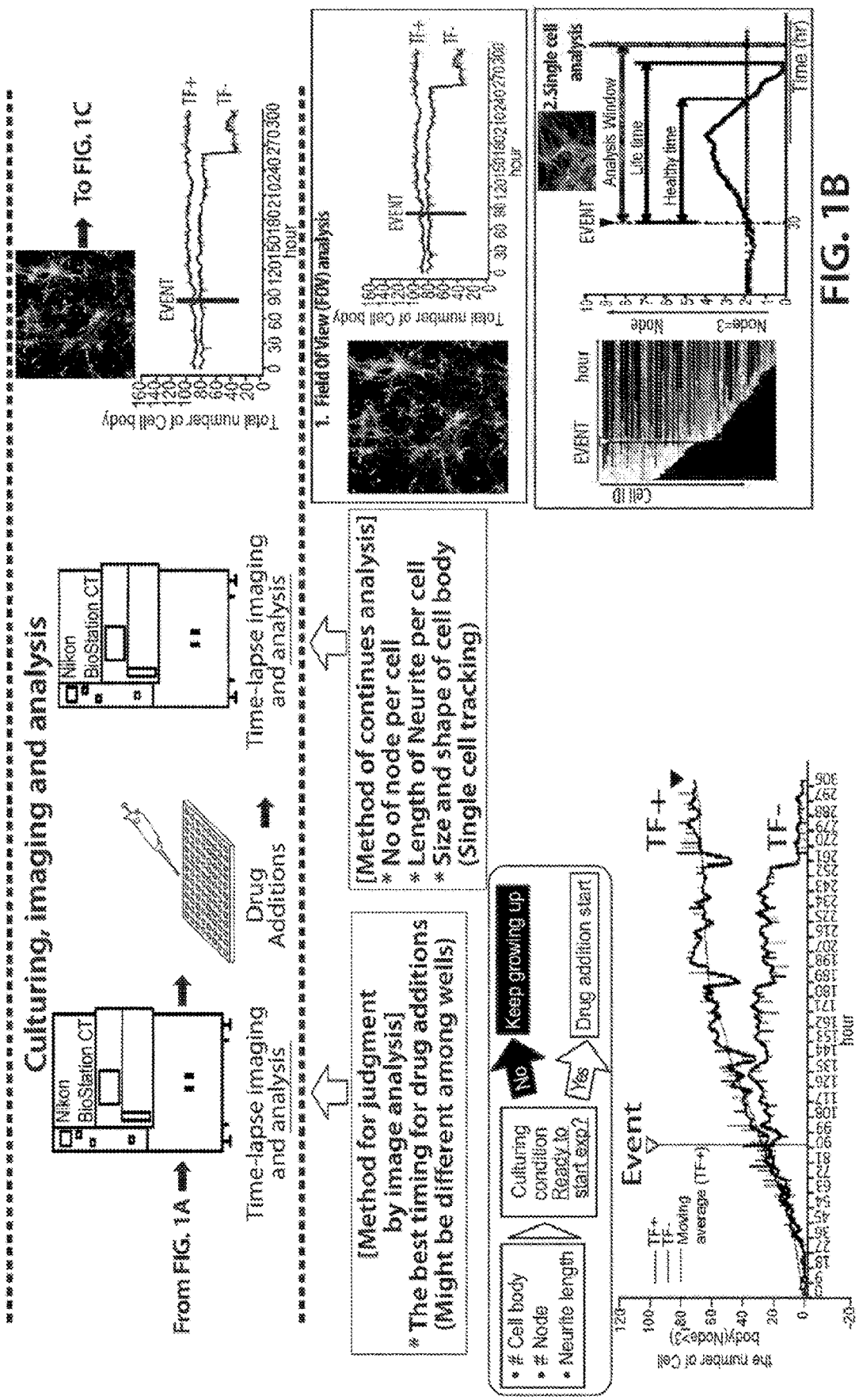
Figure 1C:
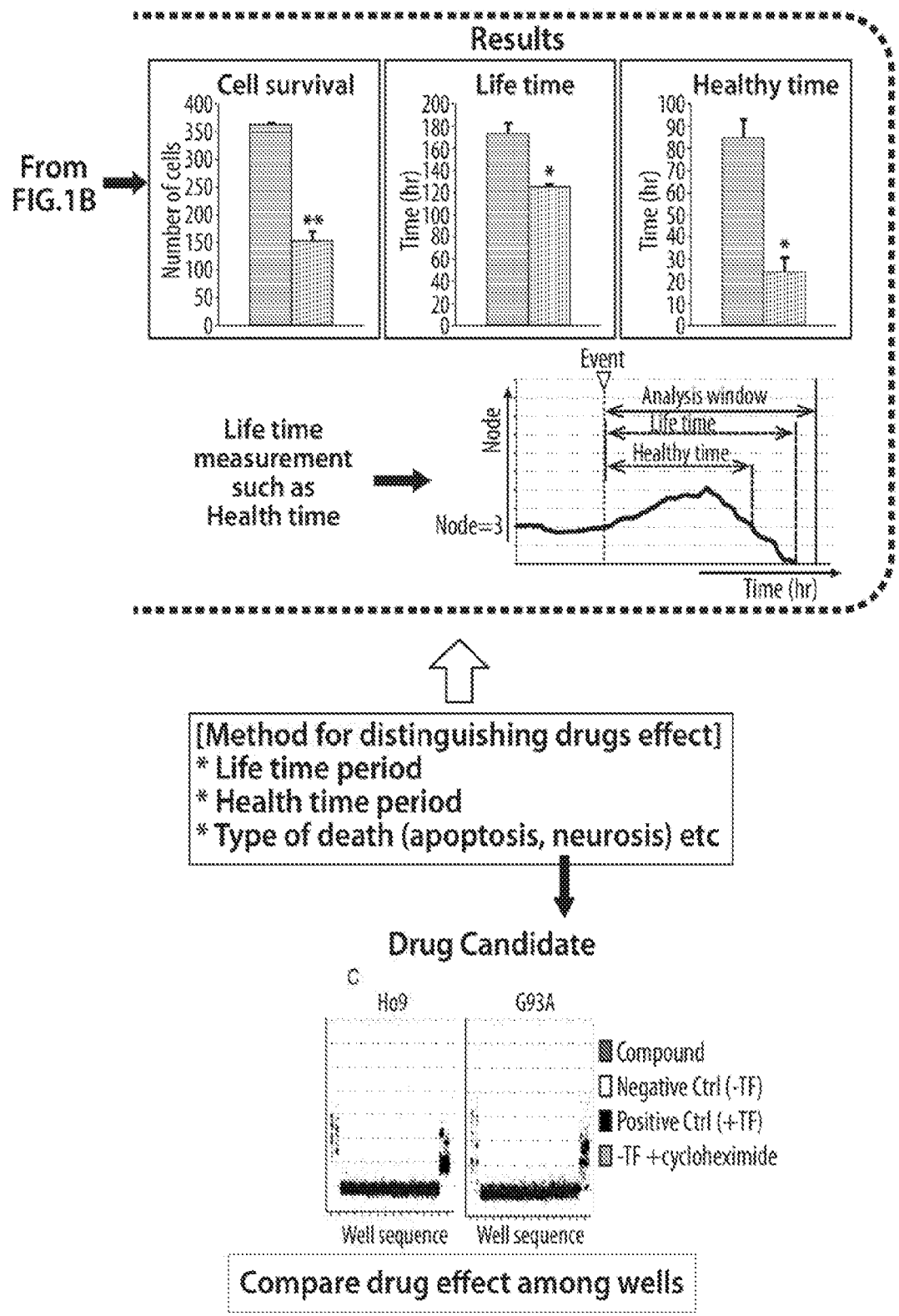

Turning more specifically to the Figures, FIGS. 1A and 6A provide schematics of non-limiting culture systems that can be used to derive motor neurons from pluripotent stem cells such as embryonic stem (ES) cells and induced pluripotent stem (iPS) cells, including patient specific iPS cells. The pluripotent stem cell sources and thus the differentiated cells can be engineered to contain a reporter gene such as green fluorescent protein (GFP) under the control of a neuronal promoter such as the Islet1 promoter. Alternatively, the motor neurons may be infected with a lentivirus that expresses a reporter gene such as red fluorescent protein (RFP) under the control of a motor neuron promoter such as synapsin promoter. Examples of both are provided herein.

In one set of experiments, on day 28 (with day 0 being the beginning of pluripotent stem cell culture), the assay may be performed. The culture times for the assay reflect time from the start of the assay and not the beginning of pluripotent stem cell culture. These time lines are shown in FIGS. 6A and B, for example. Thus, the motor neurons are grown for a first period of time during which trophic factor(s) are present. The trophic factor(s) may be BDNF, CNTF, or GDNF, or a combination of any of the foregoing. The trophic factor(s) may then be withdrawn. FIG. 6B illustrates an experimental design in which trophic factor(s) (TF) and additional supplements (B27 and N2) are withdrawn at day 4 or at day 8. TF withdrawal may be accomplished by changing the culture medium to a medium that lacks TF. The cultures may then be continued in the absence of TF, and additionally in some cultures TF may be re-introduced after a period of time. It will be understood that the withdrawal and reintroduction of TF may represent a proof-of-principle experiment, and one of ordinary skill will further recognize that other stimuli may be introduced into the culture instead of or along with TF to assess the effect of such other stimuli on motor neuron health or recovery. Similarly, the motor neurons may be stressed by withdrawal of one or more other factors or by addition of one or more stimuli. Thus, it will be clear based on this disclosure that the methods provided herein have broader applicability.

FIG. 7 illustrates the effect of early and late withdrawal of TF from motor neuron cultures (as compared to cultures that contained TF throughout the culture period) on factors such as total number of cell bodies in the culture, mean number of nodes per cell in the culture, and neurite length. It is clear that for all three measures, motor neurons that experienced an earlier TF withdrawal, and thus a longer time in culture without TF, fared worse than motor neurons that experienced a later TF withdrawal and motor neurons that experienced TF presence throughout the culture.

The analytical methods provided herein further allowed an assessment of the number of motor neurons having 0, 1, 2, 3, or 4 or more nodes. An example of these data are shown in FIG. 8. As described herein, in some instances, healthy motor neurons may be considered to be those having 3 or more nodes. The three right hand panels of FIG. 8 show the distribution of motor neurons according to node numbers when cultured in the continued presence of TF, or when experiencing early TF withdrawal or late TF withdrawal. Early TF withdrawal results in fewer cells having 3 or more nodes at later time points, as compared to continued TF presence or later TF withdrawal. Thus, as stated herein, the methods allow an end user to analyze motor neuron populations throughout the entire timeline of the experiment, rather than simply measure an end point.

As further illustrated in FIG. 6E, the methods can be used to analyze the progression of cells, at a population level or at an individual cell level, from a healthy phenotype to a healthy phenotype (HH), from a healthy phenotype to an unhealthy phenotype (HU), from a healthy phenotype to cell death (HD), or from an unhealthy phenotype to a healthy phenotype (not shown).

Figure 10:
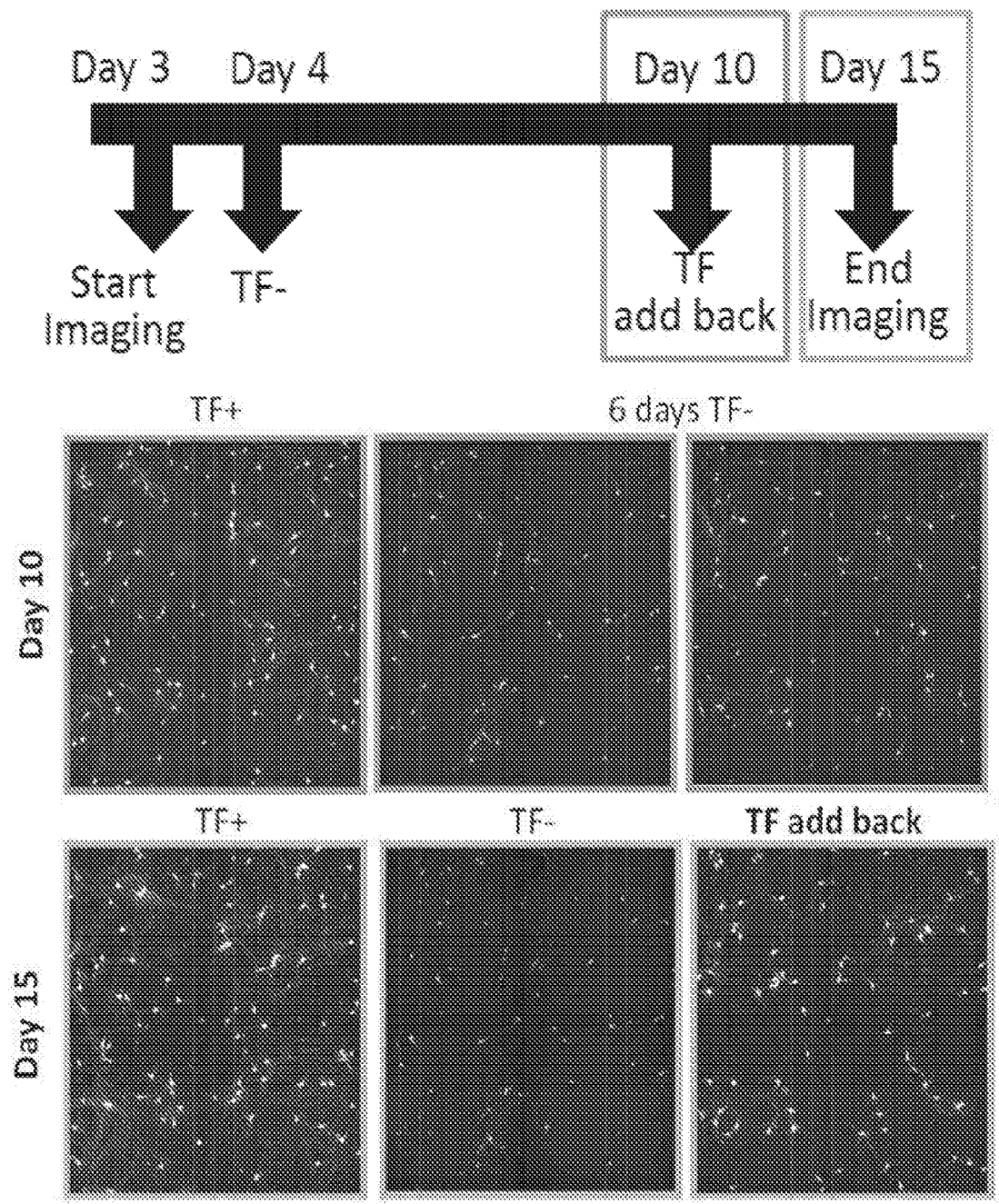
FIG. 10 illustrates the experimental design for trophic factor withdrawal and reintroduction. Human ES cells expressing GFP under the control of the Islet promoter (HUES8 Isl::GFP cells) were differentiated into MN and plated in 96-well clear bottom plates. They were imaged on the BioStation every 6 hours for 15 days. At day 4, stress was induced by the removal of trophic factor(s) (TF). At day 10, trophic factor(s) were returned to the culture medium. TF reintroduction results in substantial improvement compared to MN that remained cultured in the absence of TF. Representative images are shown and triplicate wells per condition were analyzed for each experiment.

FIG. 10 illustrates such an experimental design and provides the photographs of cell cultures at days 10 and 15 for cultures that experienced continued presence of TF (TF+), and cultures that experienced TF withdrawal from day 4 to day 15 (middle panels), and cultures that experienced TF withdrawal from day 4 to day 10 (right panels).

Figure 11:
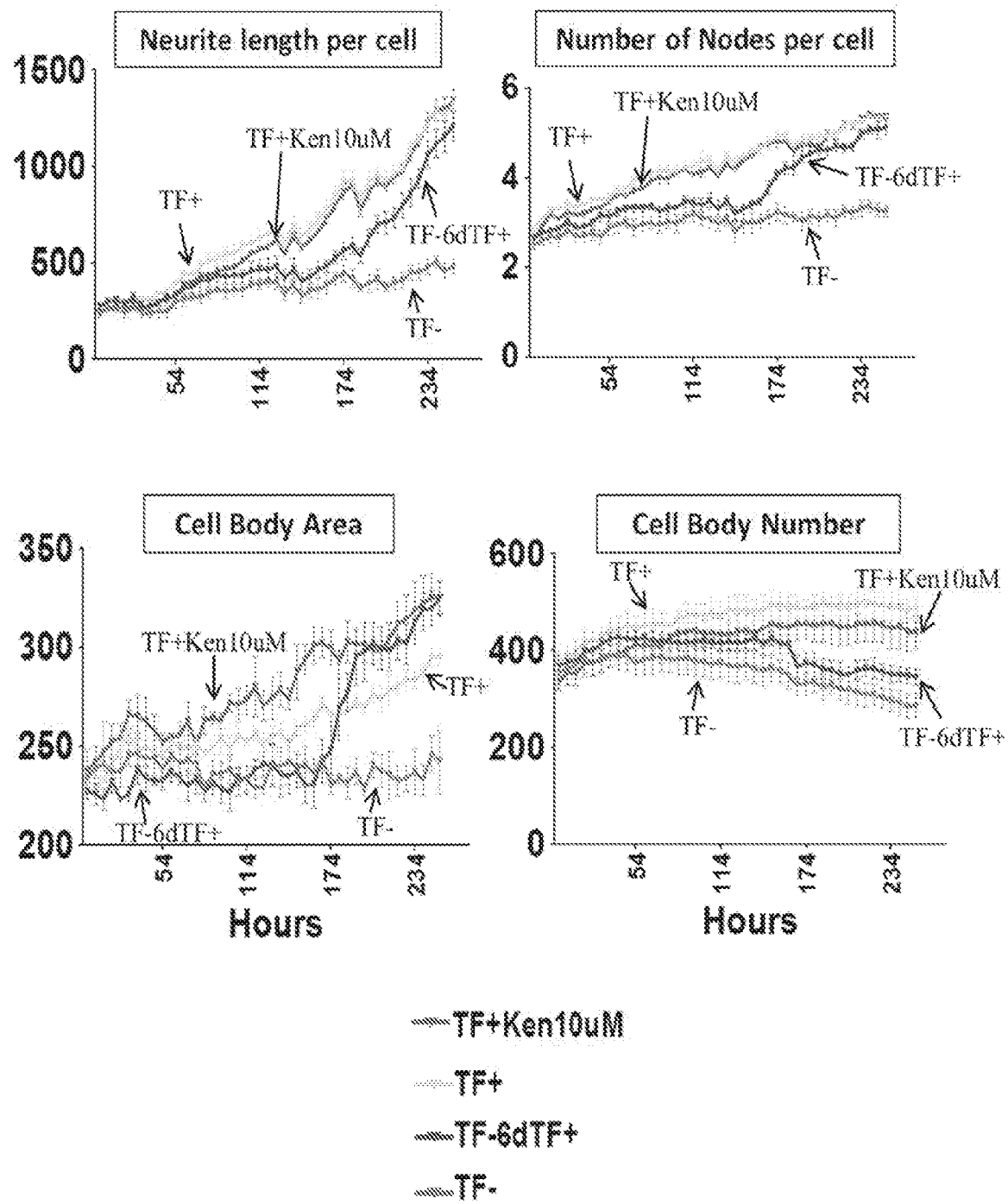
FIG. 11 shows morphological data for neurons over time and characterizes changes correlating with stress versus survival. Time plots of HUES8 Isl::GFP-derived MN for certain morphological characteristics are shown. In the control condition (TF+), the neurites grow throughout the experiment and the number of nodes (the junction between the cell body and the neurites) increased with time. Cell body area also increased with time, but at least in this line, the number of cell bodies did not change appreciably. Under the stress of TF withdrawal, growth was suppressed. However, the MN can recover if TF is returned to the culture, even after 6 days of TF withdrawal.

FIG. 11 provides time course data from a similar experiment in which cells were cultured in the presence of TF and kenpaullone (a GSK3 inhibitor), TF alone, TF withdrawal of 6 days (starting at about day 4 of culture), and complete TF absence. The methods were used to measure neurite length, number of nodes per cell, cell body area, and cell body number as a function of time for each of these culture conditions. Differences between the culture conditions are clearly apparent. In some instances, such as for cell body area, the graph demonstrates that imaging analysis throughout the culture period reveals information that would not otherwise be apparent by analyzing a culture simply at the end of the culture period.

Figure 12:
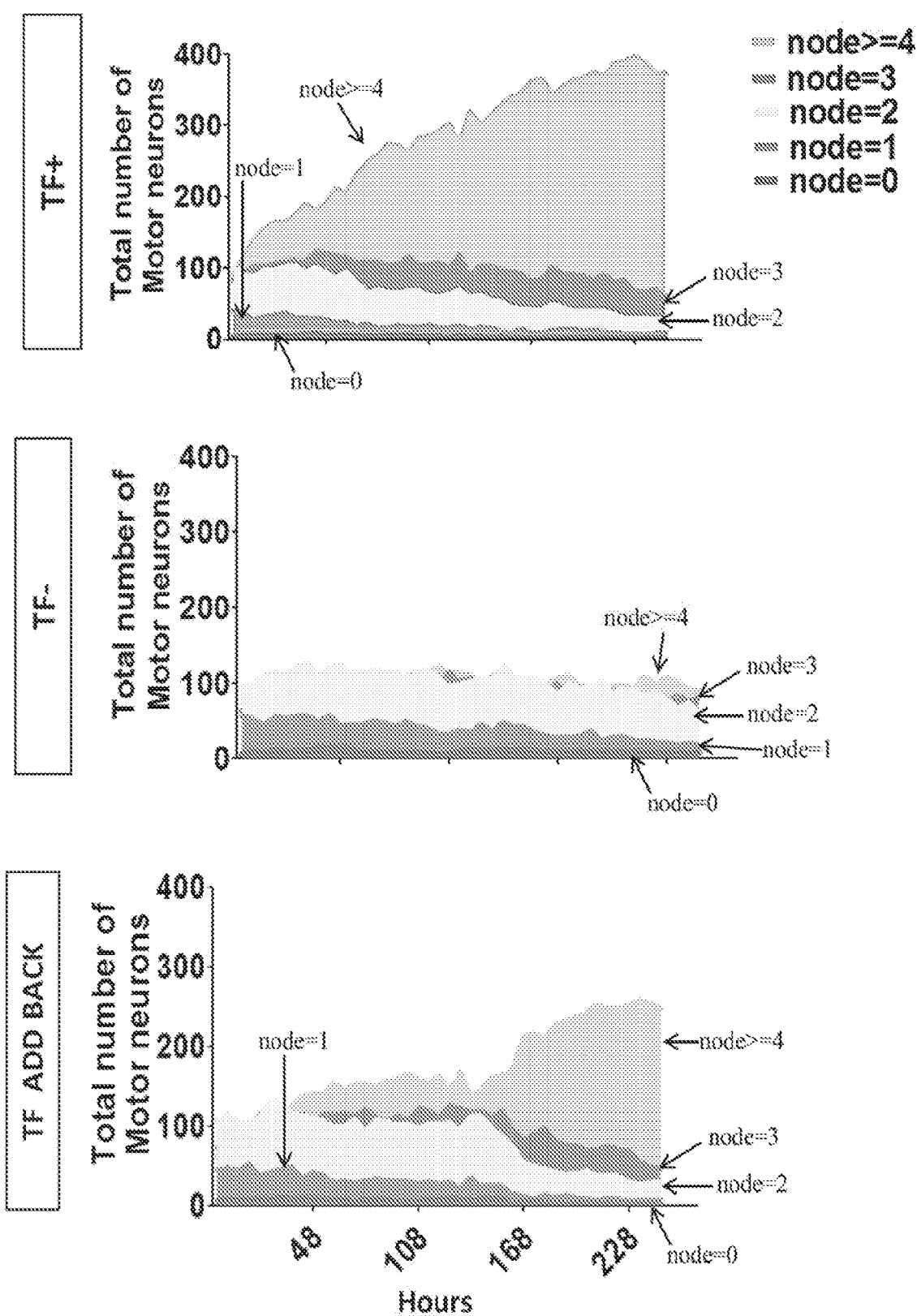
FIG. 12 shows the characterization of MN by their node number. Node plots of HUES8 Isl::GFP-derived MN are shown. For each time point, the number of MN identified with 0, 1, 2, 3, or 4 or more nodes is shown. This representation of the data shows the dramatic effect of TF- on the MN and also captures the recovery following TF reintroduction. The node information was used to divide the MN population into two categories: healthy MN defined as having 3 or more nodes and unhealthy MN have 2 or fewer nodes.

As discussed above, in various instances, the health of motor neurons is denoted by the presence of more than 3 nodes per neuron. The profile of cultures according to the distribution of cells having 0, 1, 2, 3, or 4 or more neurons is shown in FIG. 12. These plots illustrate the degree of information that can be obtained using the analytical methods provided herein. The bottom panel clearly shows the ability of TF deprived motor neurons to recover following TF reintroduction into culture. Moreover, the Figure further shows the time course of recovery. Such time course can be used to assess other stimuli on similar cultures, as for example in a screening assay.

Figure 13:
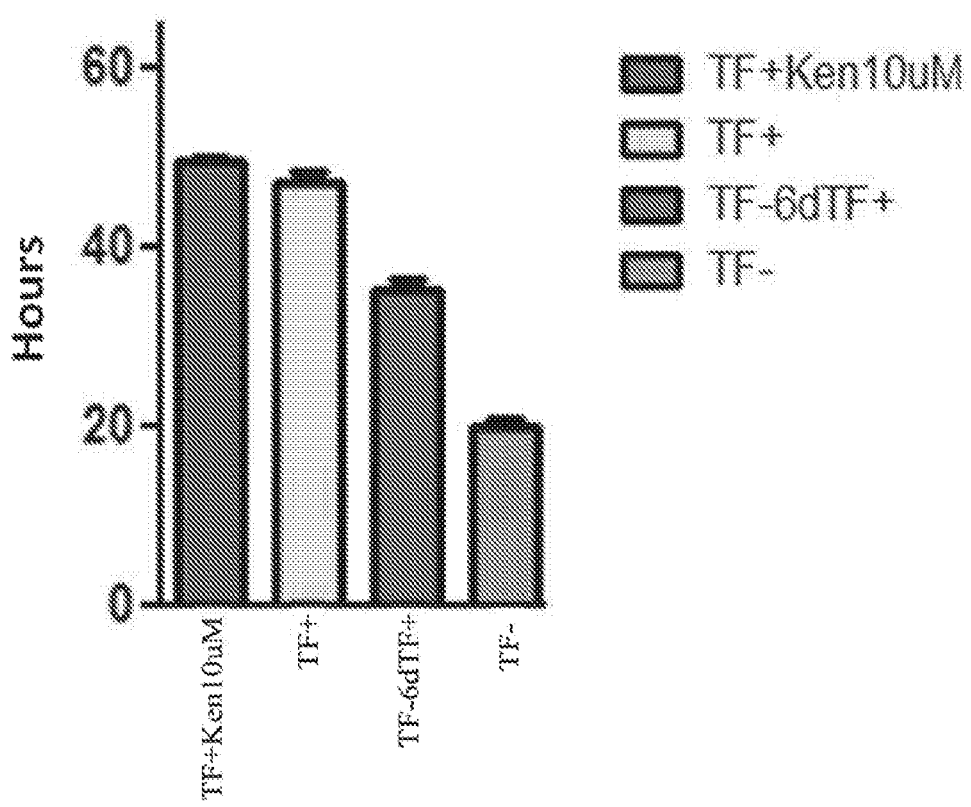
FIG. 13 illustrates "healthy time" for motor neurons under different culture conditions. Combining the node number data with single cell tracking, "Healthy Time" (HT) could be tracked on an individual cell and population basis. This is the length of time for which the MN have 3 or more nodes. Applying this to the HUES8 Isl::GFP imaging, the HT metric is consistent with the survival behaviors seen with TF withdrawal and reintroduction.
Figure 14:
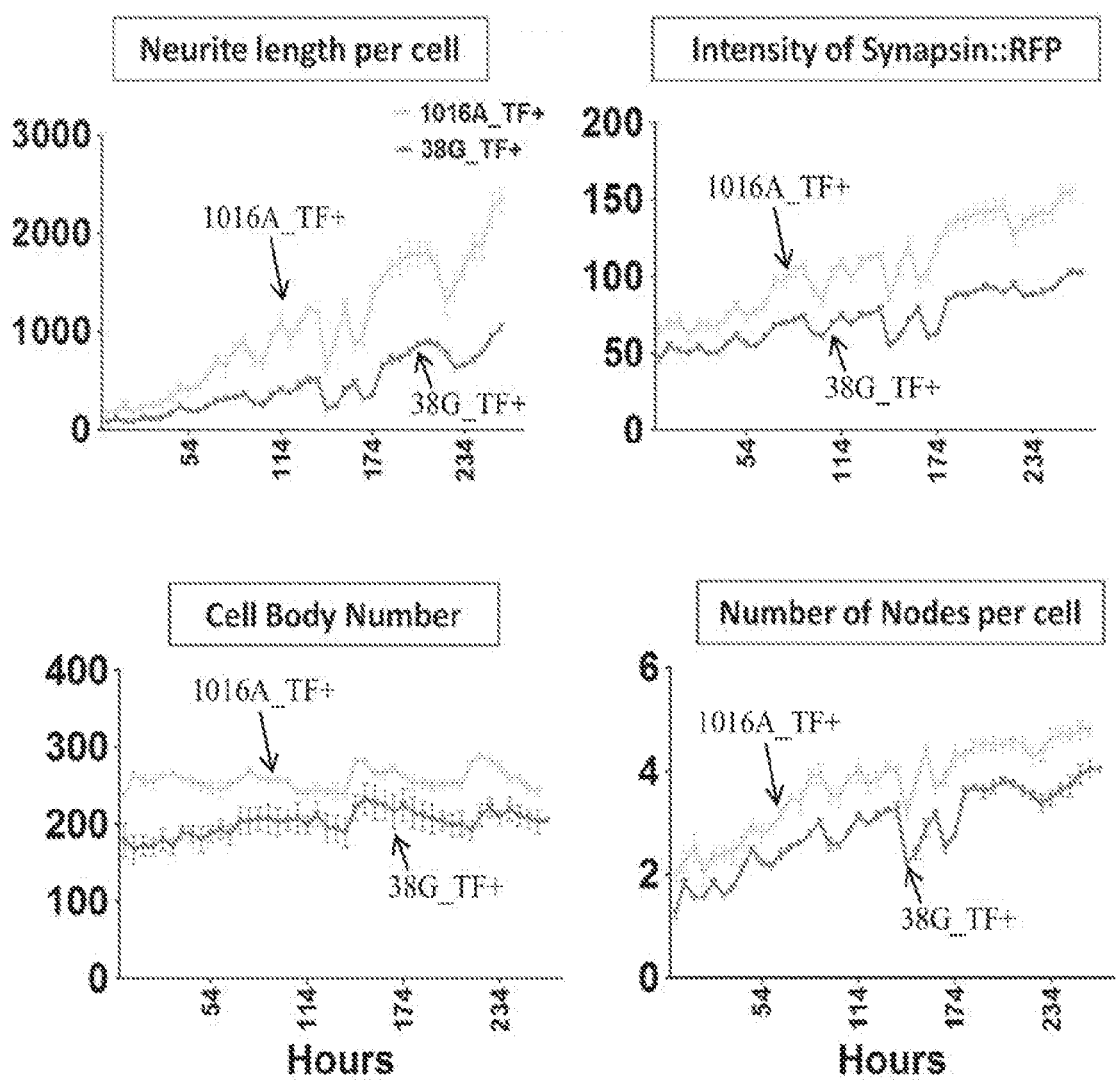
FIG. 14 shows live imaging of human iPSC-derived MN and captures morphological defects in SMA Type 1 patient MN. iPSC-derived MN cultures were treated with a lentiviral Synapsin::RFP reporter. One WT control (1016A) was compared with the Type 1 SMA patient line (1-38 G). The Type 1 SMA line exhibited multiple morphological defects under these conditions, including shorter neurites, decreased synapsin expression, fewer cell bodies, and decreased numbers of nodes, as compared to the WT control.

FIG. 13 provides the average healthy times for motor neurons cultured in the various culture conditions. Healthy time, in this instance, is the period of time in which an individual motor neuron has 3 or more nodes. This assay requires that individual neurons be tracked continually as described herein, and thus it is suited to the analytical methods provided herein.

Example 3

Figure 15:
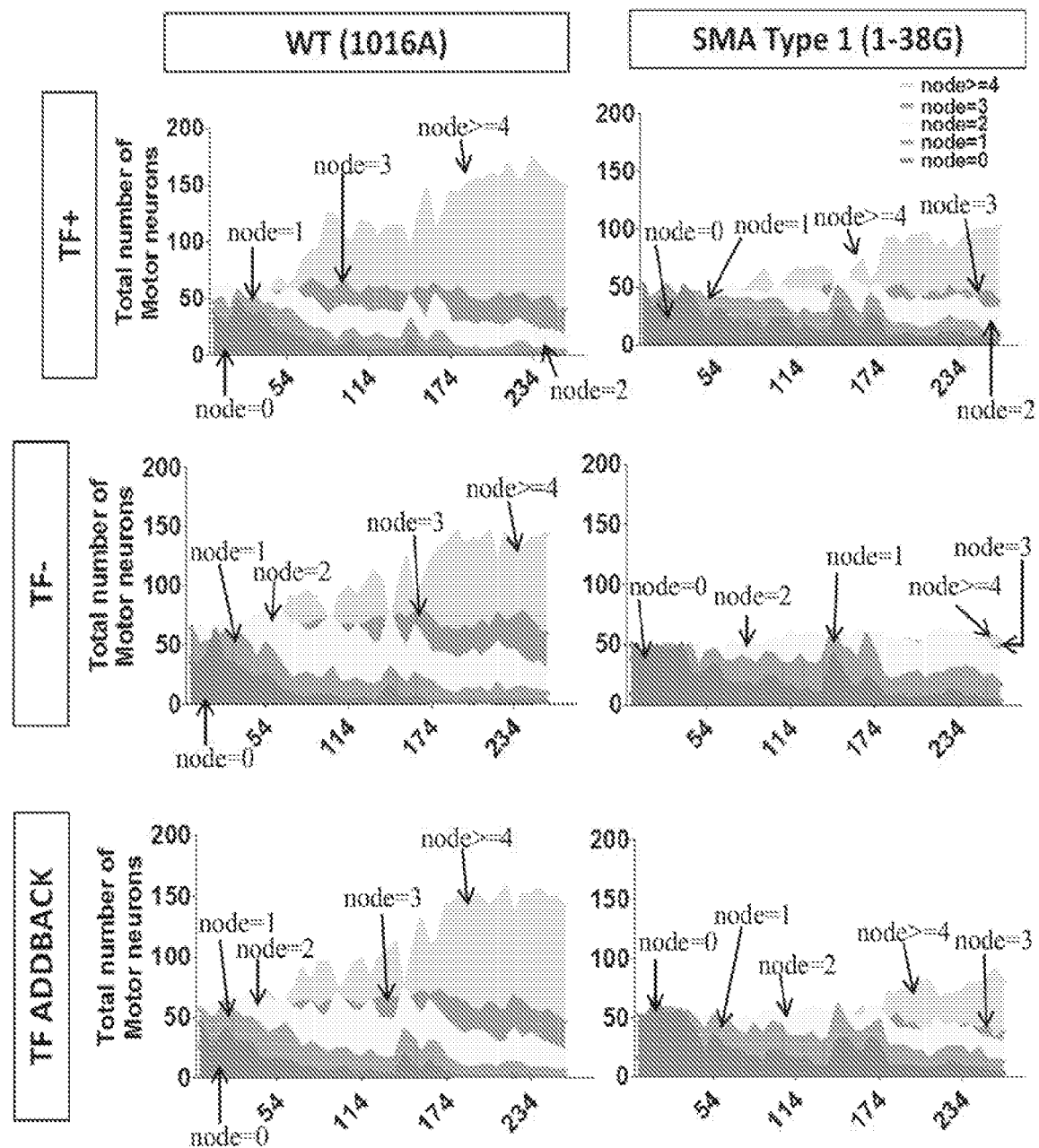
FIG. 15 illustrates that the SMA Type 1 patient MN had an abnormal node profile, had many fewer healthy MN, and was more sensitive to stress than the WT control. Further, the SMA Type 1 MN had a very strong response to the stress of TF withdrawal, yet were still able to recover upon TF reintroduction.
Figure 16:
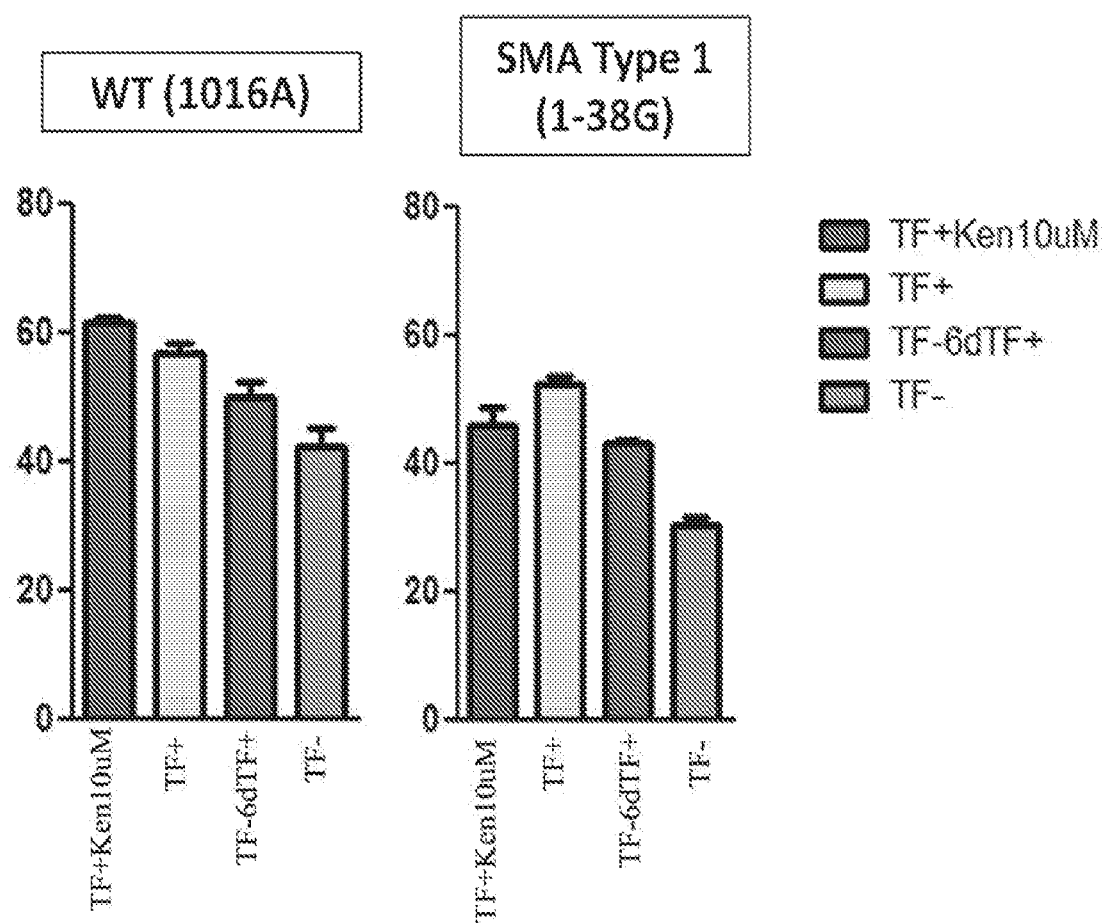
FIG. 16 illustrates that SMA Type 1 patient MN had a decreased healthy time. For all conditions tested, the SMA patient MN had a shorter Healthy Time (HT) as compared to the WT. The difference in the HT under the TF withdrawal conditions is the most striking.

FIGS. 15 and 16 provide data obtained from motor neurons derived from patient specific iPS cells. Specifically, the iPS cells were generated from an SMA type 1 patient. FIG. 15 (top row) clearly shows a marked difference between motor neurons derived from wild type iPS cells and from SMA type 1 iPS cells. The overall profile is strikingly different with the SMA type 1 motor neuron population being depleted of healthy neurons (i.e., those having 3 or more nodes) compared to wild type. Those healthy neurons were further depleted upon TF withdrawal (middle row). However, surprisingly, those same cultures are able to recover upon reintroduction of TF, as illustrated by the outgrowth of healthy neurons in the bottom row, right panel. FIG. 16 provides healthy time data for wild type motor neurons and SMA type 1 motor neurons. These data show an overall less healthy population (as evidenced by a shorter "healthy time") from the SMA type 1 cells as compared to the wild type population.

What is claimed is:

1. A method comprising
in vitro culturing a cell population using an incubator comprising an imaging device, the cell population comprising neurons;
repeatedly obtaining images of target neurons within the cell population over a period of time using the imaging device during the in vitro culturing by the incubator, either continuously or at discrete intervals of time,
detecting change in a marker in individual target neurons based on analysis of the images; and
calculating a period of time based on the detected changes in the marker,
wherein the marker includes a number of nodes per target neuron, wherein a node of a target neuron is a junction between a cell body of the target neuron and a neurite of the target neuron that extends from the cell body of the target neuron, and
wherein detecting the change in the marker in the individual neuron based on the analysis of the images comprises detecting a change in, for individual neurons of the target neurons, the number of junctions between the cell bodies and neurites of the individual neurons.

2. The method of claim 1, further comprising:
continuing the culturing the neuron population for the period of time until a percentage of target neurons having a defined phenotype is present, the defined phenotype being related to the marker.

3. The method of claim 2, wherein the defined phenotype is a healthy phenotype.

4. A method comprising
contacting target neurons in a cell culture with a stimulus, wherein the target neurons are present in a heterogeneous population of cells; and
concurrently with in vitro culturing by an incubator, the incubator comprising an imaging device:
repeatedly obtaining images of the target neurons over a period of time using the imaging device, either continuously or at discrete intervals of time,
detecting changes in a marker in individual target neurons based on analysis of the images, and
calculating a period of time based on the detected changes in the marker, and
wherein the marker includes a number of nodes per target neuron and a node of a target neuron is a junction between a cell body of the target neuron and a neurite of the target neuron that extends from the cell body of the target neuron, and
wherein detecting the changes in the marker in individual neurons based on the analysis of the images comprises detecting changes in, for individual neurons of the target neurons, the number of junctions between cell bodies and neurites of the neurons.

5. The method of claim 4, wherein detecting changes in the marker comprises
measuring the marker in the individual target neurons prior to exposure to the stimulus;
measuring the marker in the individual target neurons following contacting of the target neurons with the stimulus; and
comparing measurement of the marker from the measuring prior to exposure and the measuring following the contacting.

6. The method of claim 4, wherein detecting changes in the marker in the individual target neurons comprises:
measuring the marker post-exposure to the stimulus in individual normal cells of the target neurons;
measuring the marker post-exposure to the stimulus in individual diseased cells of the target neurons; and
comparing measurement of the marker from the measuring of the individual normal neurons and the measuring of the individual diseased neurons.

7. The method of claim 4, wherein the target neurons are obtained by in vitro differentiation of pluripotent stem cells.

8. The method of claim 7, wherein the pluripotent stem cells are induced pluripotent stem cells derived from human subjects having a neurological disorder.

9. The method of claim 4, further comprising:
monitoring the target neurons for satisfaction of at least one condition,
wherein contacting the target neurons with the stimulus comprises contacting the target neurons with the stimulus upon satisfaction of the at least one condition.

10. The method of claim 9, wherein monitoring the target neurons for satisfaction of the at least one condition comprises monitoring the target neurons for whether more than a threshold portion of the target neurons have at least one morphological characteristic.

11. The method of claim 4, further comprising:
measuring a time between when target neurons are contacted with the stimulus and when the changes in the marker are detected.

12. A determination device comprising:
at least one processor; and
at least one storage medium having encoded thereon executable instructions that, when executed by the at least one processor, cause the at least one processor to carry out a method comprising:
obtaining an image of cells in culture, the cells in culture being cultured by an incubator, the incubator comprising an imaging device, the image having been captured by the imaging device of the incubator, the cells in culture comprising neurons;
calculating a value based on a number of cell bodies of target neurons that have at least a predetermined number of nodes, out of a total number of cell bodies of target neurons depicted in an image of cells in culture, wherein each node is a junction between the cell body of a target neuron and a neurite of the target neuron;

determining whether the value satisfies a predetermined condition corresponding to a user input; and outputting information indicating a timing for administering a drug in response to determining that the value satisfies the predetermined condition.

13. The determination device according to claim 12, wherein:
the method further comprises detecting the total number of the cell bodies for the target neurons depicted in the image and a number of the nodes for each of the cell bodies of the target neurons, and calculating the value comprises calculating the value based at least in part on the total number of the cell bodies for the target neurons and the number of the nodes for each of the cell bodies of the target neurons.

14. The determination device according to claim 12, wherein the method further comprises:
storing state determination information in which a plurality of predetermined determination conditions and information indicating a state of the neurons are coordinated; and reading the state determination information and determining whether a rate of change in the value during a period of time preceding a present time by a predetermined period satisfies any of the plurality of predetermined determination conditions, wherein the outputting further comprises outputting information indicating the state of the neurons coordinated with the plurality of predetermined determination conditions satisfied by the rate of change in response to determining that the rate of change satisfies at least one of the plurality of predetermined determination conditions.

15. At least one computer-readable storage medium having encoded thereon executable instructions that, when executed by at least one processor, cause the at least one processor to carry out a method, the method comprising:
obtaining an image of neurons in culture, the neurons in culture being cultured by an incubator, the incubator comprising an imaging device, the image having been captured by the imaging device of the incubator;

calculating a value based on a number of cell bodies of target neurons that have at least a predetermined number of nodes, out of a total number of cell bodies of target neurons depicted in an image of cells in culture, and wherein each node is a junction between the cell body of a neuron and a neurite of the neuron;

determining whether the value satisfies a predetermined condition corresponding to a user input; and outputting information indicating a timing for administering a drug in response to determining that the value satisfies the predetermined condition.

16. A determination device comprising:
at least one processor; and at least one storage medium having encoded thereon executable instructions that, when executed by the at least one processor, cause the at least one processor to carry out a method comprising:
obtaining an image of cells in culture, the cells in culture comprising neurons and being cultured by an incubator, the incubator comprising an imaging device, the image having been captured by the imaging device of the incubator;

acquiring time changes in a number of nodes in individual target neurons shown in time-series images captured of the cells, wherein each of the nodes of a target neuron is a junction between a cell body of the target neuron and a neurite of the target neuron that extends from the cell body of the target neuron;

calculating a period of time from when the number of nodes becomes equal to or greater than a threshold value until the number of nodes becomes less than the threshold value, based on the time changes in the number of nodes determined in the acquiring; and outputting information indicating the period of time.

17. The determination device according to claim 16, wherein the acquiring comprises smoothing of chronological changes in the number of nodes.

18. The determination device according to claim 16, wherein
the acquiring comprises acquiring time changes in a number of the neurons, and calculating the period of time comprises calculating a period of time from when a ratio between the number of neurons determined in the acquiring and the number of neurons in which the number of nodes determined in the acquiring is equal to or greater than a threshold value becomes greater than or equal to a specified value, until it is less than the specified value, based on time changes in the number of nodes in neurons and time changes in the number of neurons determined in the acquiring.

19. The determination device according to claim 16, wherein:
the method further comprises detecting nodes in the neurons from the time-series images captured of the neurons, and the acquiring further comprises acquiring time changes in the number of nodes detected in the detecting.

20. A neuron production method comprising the steps of:
obtaining time-series images of cells in culture, the cells in culture being cultured by an incubator and comprising neurons, the incubator comprising an imaging device, the image having been captured by the imaging device of the incubator;

acquiring time changes in a number of nodes in individual neurons shown in the time-series images captured of the cells in culture, wherein each of the nodes of a target neuron is a junction between a cell body of the target neuron and a neurite of the target neuron that extends from the cell body of the target neuron;

calculating a period of time from when the number of nodes becomes equal to or greater than a threshold value until it becomes less than the threshold value, based on the acquired time changes in the number nodes;

outputting information indicating the calculated period of time; and implementing treatment to produce changes in the neurons based on the output information.

21. A neuron produced by the neuron production method according to claim 20.

22. The determination device of claim 12, wherein:
the determination device comprises the incubator and the imaging device; and obtaining the image comprises capturing the image with the imaging device.

23. The at least one computer-readable storage medium of claim 15, wherein obtaining the image comprises capturing the image with the imaging device.

24. The determination device of claim 16, wherein:

the determination device comprises the incubator and the imaging device; and obtaining the image comprises capturing the image with the imaging device.

25. The determination device of claim 13, wherein:

the cells in culture comprise neurons; and detecting the number of the nodes for each of the cell bodies comprises, for each neuron, determining a number of locations between a cell body of the neuron and a neurite of the neuron.

26. The determination device of claim 13, wherein:

the cells in culture comprise neurons; and detecting the number of the nodes for each of the cell bodies comprises, for each neuron, determining a number of neurites extending from a cell body of the neuron.

* * * * *